US005559008A

United States Patent [19]

Chang

[11] Patent Number: 5,559,008

[45] Date of Patent: Sep. 24, 1996

[54] LEUKOTOXIN GENE FROM *PASTEURELLA SUIS*

[75] Inventor: Yung-Fu Chang, Ithaca, N.Y.

[73] Assignee: Cornell Research Foundation, Inc., Ithaca, N.Y.

[21] Appl. No.: 215,805

[22] Filed: Mar. 22, 1994

Related U.S. Application Data

[62] Division of Ser. No. 972,157, Nov. 5, 1992, abandoned.

[51] Int. Cl.[6] .............................. C12N 15/31; C12N 1/13; C12N 1/19; C12P 21/02

[52] U.S. Cl. ........................ 435/69.1; 536/23.7; 435/69.3; 435/240.1; 435/252.3; 435/252.33; 435/254.11; 435/320.1

[58] Field of Search ........................ 536/23.7; 435/320.1, 435/252.3, 252.33, 240.1, 240.2, 240.4, 254.11, 69.1, 69.3, 172.3; 935/11, 12, 65

[56] References Cited

PUBLICATIONS

Burrows, L. et al. 1992, Infect. Immun. vol. 60 pp. 2166–2173.

Highlander, S. K. et al. 1989. DNA vol. 8 pp. 15–28.

Lo, R.C. 1990. Can. J. Vet. Res. vol. 54 pp. 533–535.

McWhinney et al., "Separable Domains Define Target Cell Specificities of an RTX Hemolysin from *Actinobacillus pleuropneumoniae,*" 1992, J. Bacteriol., vol. 174, pp. 291–297.

Felmleel et al., "Nucleotide Sequence of an *Escherichia coli* Chromosomal Hemolysin," 1985, J. Bacteriol., vol. 163, pp. 94–105.

Highlander et al., "Secretion and Expression of *Pasteurella haemolytica* leukotoxin," 1990, J. Bacteriol., vol. 172, pp. 2343–2350.

Mackman et al., "Genetical and Functional Organization of the *Escherichia coli* Haemolysin Determinant 2001," 1985, Mol. Gen. Genet., vol. 201, pp. 282–288.

Chang et al., "The *Actinobacillus pleuropneumoniae* Hemolysin Determinant: Unlinked appCA and appBD Loci Flanked by Pseudogenes", 1991, J. Bacteriol, vol. 173, pp. 5151–5158.

Oberst et al., "Further Characterization of *Pasteurella haemolytica*–Like Bacteria Isolated from Swine Enteritia," 1993 vet. Microbiol., vol. 34, 287–302.

Frey et al., "Nucleotide Sequence of the Hemolysin I gene from *Actinobacillus pleuropneumoniae,*" 1991, Infect. & Immun. vol. 59, pp. 3026–3032.

Chang et al., "Molecular Characterization of a Leukotoxin Gene from a *Pasteurella haemolytica*–like Organism, Encoding a New Member of the RTX Toxin Family", 1993, Infect. & Immunity, vol. 61, pp. 2089–2095.

Chang et al., "Molecular Analysis of the *Actinobacillus pleuropneumoniae* RTX Toxin–III Gene Cluster," 1993, DNA and Cell Biology, vol. 12, pp. 351–362.

Devenish et al., "Immunoserological comparison of 104–Kilodalton Proteins Associated with Hemolysis and Cytolysis in *Actinobacillus pleuropneumoniae, Actinobacillus suis, Pasteurella haemolytica,* and *Escherichia coli,*" 1989, Infect & Immunity, vol. 57, pp. 3210–3213.

Russell and Bennett, "Construction and analysis of in vivo activity of *E.coli* promoter hybrids and promoter mutants that alter the –35 to –10 spacing," 1982, Gene vol. 20, pp. 231–243.

Hunkapiller et al., "A microchemical facility for the analysis and synthesis of genes and proteins," 1984, Nature, vol. 310, pp. 105–111.

Chang et al., "Identification and Characterization of the *Pasteurella haemolytica* Leukotoxin", 1987, Infect. & Immun., vol. 55, pp. 2348–2354.

Chengappa et al., "Improved Method for Obtaining Streptomycin–Dependent Mutants from *Pasteurella multocida* and *Pasteurella haemolytica,* using N–methyl–N'nitrosoquanidine", 1979, Am. J. Vet. Res., vol. 40, pp. 449–450.

Miller, J. H., "Experiments in Molecular Genetics", 1972, p. 433, Cold Spring Harbor Laboratory Press, Cold Spring Harbor, NY.

Messing, J., "New M13 Vectors for Cloning", 1983, Methods in Enzymol., vol. 101, pp. 20–78.

Welch et al., "Transcriptional Organization of the *Escherichia coli* Hemolysin Genes", 1988, J. Bacteriol, vol. 170, pp. 1622–1630.

Silhavy et al., "Experiments in Gene Fusions", 1984, pp. 89–90, Cold Spring Harbor Laboratory Press, Cold Spring Harbor, N.Y.

Sanger et al., "DNA Sequencing with Chain–Terminating Inhibitors", 1977, Proc. Natl. Acad. Sci. USA, vol. 74, pp. 5463–5467

Pearson and Lipman, "Improved Tools for Biological Sequence Comparison", 1988, Proc. Natl. Acad. Sci. USA, vol. 85, pp. 2444–2448.

Buschmann and Pawlas, "A Study of Porcine Lymphocyte Populations: Separation of Porcine Lymphocyte Subpopulations" 1980, Vet. Immun. Immunopath., vol. 1, pp. 215–224.

Mulligan et al., "*Escherichia coli* promoter sequences predict in vitro RNA polymerase selectivity", 1984, Nucl. Acid Res., vol. 12, PP. 789–800.

(List continued on next page.)

*Primary Examiner*—Mary E. Mosher

*Attorney, Agent, or Firm*—Nixon, Hargrave, Devans & Doyle

[57] ABSTRACT

The present invention discloses a new species of gram-negative bacterium, designated "*Pasteurella suis,*" isolated from piglets with diarrhea, a gene or gene fragment encoding a novel leukotoxin secreted from *Pasteurella suis*, recombinant DNA sequences and expression systems for directing expression of the gene, a method of using the gene or gene fragment as an immunogen in vaccine formulations and as reagents in diagnostic assays.

36 Claims, 10 Drawing Sheets

OTHER PUBLICATIONS

Klein et al., "The Detection and Classification of Membrane–Spanning Proteins", 1985, Biochim. Biophys. Acta, vol. 815, pp. 486–476.

Stewart et al., "pHG165:A pBR322 Copy Number Derivative pf pUC8 for Cloning and Expression", 1986, Plasmid, vol. 15, pp. 172–181.

Lo et al., "Nucleotide Sequence of the Leukotoxin Genes of *Pasteurella haemolytica* A1", 1987, Infect. & Immun., vol. 55, pp. 1987–1996.

Kraig et al., "Nucleotide Sequence of the Leukotoxin Gene From *Actinobacillus actinomycetemcomitans:* Homology to the Alpha–Hemolysin/Leukotoxin Gene Family", 1990, Infect. & Immun., vol. 58, pp. 920–929.

Lally et al., "Analysis of the *Actinobacillus actinomycetemcomitans* Leukotoxin Gene", 1989, J. Biol. Chem., vol. 264, pp. 15451–15456.

Chang et al., "Characterization of Plasmids with Antimicrobial Resistant Genes in *Pasteurella haemolytica* A1", 1992, DNA Sequence–J. DNA Sequencing and Mapping, vol. 3, pp. 89–97.

Burrows and Lo, "Molecular Characterization of an RTX Toxin Determinant from *Actinobacillus suis*" 1992, Infect & Immunity, vol. 60, pp. 2166–2173.

Lally et al., "Structure and function of the B and D genes of the *Actinobacillus actinomycetemcomitans* leukotoxin complex," 1991, Microbial Pathogenesis, vol. 11, pp. 111–121.

Thompson et al., "*Neisseria meningitidis* Produces Iron–Regulated Proteins Related to the RTX Family of Exoproteins," 1993, J Bacteriology, vol. 175, pp. 811–818.

Chang et al., "Cloning and Characterization of a Hemolysin Gene from *Actinobacillus (Haemophilus) pleuropneumoniae,*" 1989, DNA, vol. 8, pp. 635–647.

McLaughlin et al., "Association of a *Pasteurella haemolytica*–like organism with enteritis in swine," 1991, J Vet Diagn Invest, vol. 3, pp. 324–327.

FIG. 3A

```
380                                    -360                              -340        -
GGCAGCATTAATCCTGGAGGCTTAAACTTAAAATTAAGTGGTCTGATTCTTGCAAAATTT
320                                    -300                              -280        -
GCACAAATCAGACCGCTGTATTTTATTTAGCACTCATCTCTTTATTGTAAAATTTTATCC
260                                    -240                              -220        -
TTACAAAACGATACCTATCTCTTAAACTTTCTTAAATAAAATGAAAAGCAAATATTACAT
200                                    -180                              -160        -
TAATTTTACAATGTAATTATTTTGTTTATTTTTCGGCATTTGTGTAACTTTAAAGTATTT
140                                    -120                              -100
TATTTTGCAATTAATTTACATGAAAGGCAAAAAACACAATTAAAACAATTAAAACAATAA
-80                                    -60                               -40
AAAATCCTGTGGTAAGATCAGTTGATTAATATATTATGCTAAAATTTTGATTCTAATCTA
                                      ^^^^^^                      ^^^^^^

-20                                    1                         20
GAATCATTATCGAGTGTGAATTATGAATCAACATTACTTTAATCTATTGGAAATATTAC
                                       M  N  Q  H  Y  F  N  L  L  G  N  I  T
40                          60                            80                          1
TTGGTTATGGATGAACTCACCTCTTCATAGAGAGTGGAGCTGTGAGCTATTGGCACGCAA
 W  L  W  M  N  S  P  L  H  R  E  W  S  C  E  L  L  A  R  N
00                          120                           140                         1
TGTGATTCCGGCAATTGAAAATCAACAATATATGCTACTTATTGATAATGATGTTCCAAT
 V  I  P  A  I  E  N  Q  Q  Y  M  L  L  I  D  N  D  V  P  I
60                          180                           200                         2
CGCATATTGCAGTTGGGCAGATTTAAGCCTTGAGACTGAAGTAAAGTATATTAAGGATAT
 A  Y  C  S  W  A  D  L  S  L  E  T  E  V  K  Y  I  K  D  I
20                          240                           260                         2
TAGTTCATTAACACCGGAAGAATGGCAGTCTGGCGATAGACGTTGGATTATTGATTGGGT
 S  S  L  T  P  E  E  W  Q  S  G  D  R  R  W  I  I  D  W  V
```

FIG. 3B

```
80                         300                         320                         3
AGCACCATTCGGGCATTCTCAACTACTTATAAAAAATGTGTCAGAAATACCTGATTACTC
  A  P  F  G  H  S  Q  L  L  I  K  N  V  S  E  I  P  D  Y  S
40                         360                         380                         4
TCGTCAGATCTATACGCTTTTATCCAAAACAAAAAGAACTGGCAAAATTGCCTATTTTAA
  R  Q  I  Y  T  L  L  S  K  T  K  R  T  G  K  I  A  Y  F  K
00                         420                         440                         4
AGGGGGAACTTAGATAAAAAAACAGCAAAAAAACGTTTCGATACATATCAAGAAAGGCT
  G  G  N  L  D  K  K  T  A  K  K  R  F  D  T  Y  Q  E  R  L
60                         480                         500                         5
GGGGGCAGCTCTTAAAAATGAGTTTAATTTTACTAAATAAAAGGAGACATCCTTATGGGT
  G  A  A  L  K  N  E  F  N  F  T  K                    M  G
20                         540                         560                         5
AAACTTGCTAATATTTCAACAAACTTAAAAAATTCATTGCAATCCGGTTTGCATAAAACA
 K  L  A  N  I  S  T  N  L  K  N  S  L  Q  S  G  L  H  K  T
80                         600                         620                         6
GGGCAATCTTTAAACCAAGCCGGTCAATCTTTAAAAGCCGGAGCGAAAAAGCTCATTCTC
 G  Q  S  L  N  Q  A  G  Q  S  L  K  A  G  A  K  K  L  I  L
40                         660                         680                         6
TATATTCCAAAAGATTATGAATATGATTCAGGAAGAGGAAACGGTTTACAGGATTTAGTC
 Y  I  P  K  D  Y  E  Y  D  S  G  R  G  N  G  L  Q  D  L  V
00                         720                         740                         7
AAAGCTGCAGAAGATTTAGGTATTGAAGTACAAAGAGAAGAGCGTAATGGTATTGCTACC
 K  A  A  E  D  L  G  I  E  V  Q  R  E  E  R  N  G  I  A  T
```

FIG. 3C

```
60                     780                       800                      8
GCTCAAAACAGTTTAAGTACAATTCAAAATATTCTTGGGTTTAGCGAGCGTGGAGTTGTA
 A  Q  N  S  L  S  T  I  Q  N  I  L  G  F  S  E  R  G  V  V
20                     840                       860                      8
TTGTCTGCTCCTCAACTTGATAAACTGCTTCAAAAATACAAAATCAGTAAAGCACCAGGT
 L  S  A  P  Q  L  D  K  L  L  Q  K  Y  K  I  S  K  A  P  G
80                     900                       920                      9
TCATCAGAAAATGTAGCTAAAAATTTGGGTAATGCACAAACTTTATTATCGGGTATTCAA
 S  S  E  N  V  A  K  N  L  G  N  A  Q  T  L  L  S  G  I  Q
40                     960                       980                     10
TCTATTTTAGGCTCAGTCATGGCCGGTATGGATTTAGATGAAATCTTGAAAAATAAAGGA
 S  I  L  G  S  V  M  A  G  M  D  L  D  E  I  L  K  N  K  G
00                    1020                      1040                     10
AGTGAACTTGATTTAGCAAAAGCTGGTTTAGAATTAACTAATTCGTTAATTGAAAATATT
 S  E  L  D  L  A  K  A  G  L  E  L  T  N  S  L  I  E  N  I
60                    1080                      1100                     11
GCAAATTCTGTTCAAACGCTTGATACTTTTTCAGAACAAATTAGCCAATTAGGTACTAAG
 A  N  S  V  Q  T  L  D  T  F  S  E  Q  I  S  Q  L  G  T  K
20                    1140                      1160                     11
TTACAAAATGTAAAAGGTTTAGGTACTTTAGGAGATAAACTTAAAAACTTTAGTGGCTTC
 L  Q  N  V  K  G  L  G  T  L  G  D  K  L  K  N  F  S  G  F
80                    1200                      1220                     12
AGTAAAGCTGGTCTTGGCTTAGAAGTAATTTCCGGTTTGCTTTCTGGTGCAACAGCAGCT
 S  K  A  G  L  G  L  E  V  I  S  G  L  L  S  G  A  T  A  A
40                    1260                      1280                     13
CTTGTTCTTGCAGATAAAAATGCCTCTACAGATAGGAAAGTAGGTGCTGGCTTTGAGCTC
 L  V  L  A  D  K  N  A  S  T  D  R  K  V  G  A  G  F  E  L
00                    1320                      1340                     13
GCAAACCAAGTTGTTGGTAACATCACCAAAGCCGTTTCCTCTTATATTTTAGCACAGCGT
 A  N  Q  V  V  G  N  I  T  K  A  V  S  S  Y  I  L  A  Q  R
```

FIG. 3D

```
60                 1380                          1400                          14
GTTGCCGCGGGTTTATCTAATACAGGCCCAGTGTCAGCATTAATTGCTTCTACTGTAGCA
 V  A  A  G  L  S  N  T  G  P  V  S  A  L  I  A  S  T  V  A
20                 1440                          1460                          14
CTTGCTATTAGTCCGCTTGCCTTTGCAGGAATTGCAGATAAATTTAACAATGCTAAAGCA
 L  A  I  S  P  L  A  F  A  G  I  A  D  K  F  N  N  A  K  A
80                 1500                          1520                          15
CTTGAAAGTTATGCAGAGAGATTTAAAAAACTAGGCTATGAGGGGGATAGTTTACTCGCT
 L  E  S  Y  A  E  R  F  K  K  L  G  Y  E  G  D  S  L  L  A
40                 1560                          1580                          16
GAATATCAACGAGGAACAGGTACGATAGATGCTTCTGTAACCGCGGTTAATACTGCATTA
 E  Y  Q  R  G  T  G  T  I  D  A  S  V  T  A  V  N  T  A  L
00                 1620                          1640                          16
GCTGCAATTTCAGGTGGCGTTTCAGCCGCAGCAGCCGGTTCTCTAGTCGGCGCACCGATT
 A  A  I  S  G  G  V  S  A  A  A  A  G  S  L  V  G  A  P  I
60                 1680                          1700                          17
GCTCTACTTGTTTCTGGTATCACCGGAATTATCTCAACTATTCTACAATACTCTAAACAA
 A  L  L  V  S  G  I  T  G  I  I  S  T  I  L  Q  Y  S  K  Q
20                 1740                          1760                          17
GCGATGTTTGAGCATGTAGCGAATAAAATTCACGATAAAATTGTGGATTGGGAGAAAAAA
 A  M  F  E  H  V  A  N  K  I  H  D  K  I  V  D  W  E  K  K
80                 1800                          1820                          18
CATAACGGCAAAAACTACTTCGAAAATGGTTATGACTCTCGCTATTTAGCCGATCTTCAA
 H  N  G  K  N  Y  F  E  N  G  Y  D  S  R  Y  L  A  D  L  Q
```

FIG. 3E

```
40                  1860                 1880                19
GACAATATGCGTCAGTTACAGAATCTCAATAAAGAACTACAAGCAGAACGTGTTATCCGG
 D  N  M  R  Q  L  Q  N  L  N  K  E  L  Q  A  E  R  V  I  R
00                  1920                 1940                19
ATTACGCAACAGCAATGGGATAATAATATTGGTAACCTGGCTGGTATCAGCCGATTAGGT
 I  T  Q  Q  Q  W  D  N  N  I  G  N  L  A  G  I  S  R  L  G
60                  1980                 2000                20
GAAAAAGTAATGAGCGGAAAAGCTTATGCAGATGCTTTTGAAGAAGGCAAACTCATAAAA
 E  K  V  M  S  G  K  A  Y  A  D  A  F  E  E  G  K  L  I  K
20                  2040                 2060                20
GCAGATACATTTGTACAATTAGATTCTGCCACAGGGGTGATCAATACTAGCAAGTCTGAT
 A  D  T  F  V  Q  L  D  S  A  T  G  V  I  N  T  S  K  S  D
80                  2100                 2120                21
AATGTTAAAACTCAGCATATTTTATTTAGAACGCCACTACTTACCCCAGGGGTAGAAAAT
 N  V  K  T  Q  H  I  L  F  R  T  P  L  L  T  P  G  V  E  N
40                  2160                 2180                22
CGTGAGCGTATTCAAACTGGTAAATATGAGTATATTACCAAATTAAATATTAACCGTGTA
 R  E  R  I  Q  T  G  K  Y  E  Y  I  T  K  L  N  I  N  R  V
00                  2220                 2240                22
GACAGCTGGAAAATTACTGATGGAGCTACAAACTCTACCTTTGACTTGACTAATGTGGTT
 D  S  W  K  I  T  D  G  A  T  N  S  T  F  D  L  T  N  V  V
60                  2280                 2300                23
CAACGTATTGGTATTGAATTAGATCACGCAGATAATGTTACTAAAACAAAAGAGACTAAA
 Q  R  I  G  I  E  L  D  H  A  D  N  V  T  K  T  K  E  T  K
20                  2340                 2360                23
ATTATTGCAAATCTAGGTGATGGCAATGATGATGTATTTATTGGTTCAGGCACAACTGAA
 I  I  A  N  L  G  D  G  N  D  D  V  F  I  G  S  G  T  T  E
```

FIG. 3F

```
80                      2400                      2420                     24
GTTGATGGTGGTAACGGTCTTGATCGCGTGCATTATAGCCGAGGCGACTACGGTGCATTA
 V   D   G   G   N   G   L   D   R   V   H   Y   S   R   G   D   Y   G   A   L
40                      2460                      2480                     25
ACTATTGATGCAACGAATGAATCAGTCCAAGGTAGTTATACAGTTAAGCGTTTCGTTGAA
 T   I   D   A   T   N   E   S   V   Q   G   S   Y   T   V   K   R   F   V   E
00                      2520                      2540                     25
ACTGGTAAAGCATTGCATGAAGTAACTGCAACTCAATCTGTTTTAGTTGGTAGCCGCGAA
 T   G   K   A   L   H   E   V   T   A   T   Q   S   V   L   V   G   S   R   E
60                      2580                      2600                     26
GAAAAAATTGAGTATCGTCACAGTAATAATACACAGCATGCTGGTTACTATACTACAGAT
 E   K   I   E   Y   R   H   S   N   N   T   Q   H   A   G   Y   Y   T   T   D
20                      2640                      2660                     26
ACTTTAAAGTCTGTTGAGGAAATTATTGGTACTTCACGCAATGATATCTTTAAAGGTAGT
 T   L   K   S   V   E   E   I   I   G   T   S   R   N   D   I   F   K   G   S
80                      2700                      2720                     27
AAATTTGATGATGCTTTCCATGGCGGTGATGGTGTTGATAACATTGACGGTAATGCAGGC
 K   F   D   D   A   F   H   G   G   D   G   V   D   N   I   D   G   N   A   G
40                      2760                      2780                     28
AATGACCGTCTATTTGGCGGAAAAGGCTTTGATATTATTGATGGCGGTGATGGTGATGAC
 N   D   R   L   F   G   G   K   G   F   D   I   I   D   G   G   D   G   D   D
00                      2820                      2840                     28
TTTATCGATGGCGGTCAAGGAGATGATATCTTACACGGCGGCAAAGGCAATGATATCTTG
 F   I   D   G   G   Q   G   D   D   I   L   H   G   G   K   G   N   D   I   L
60                      2880                      2900                     29
TGCACCGTCAAGGGTGGCAATGATTCAATTAGCGACTCTGGCGGCAATGATAGATTATCT
 C   T   V   K   G   G   N   D   S   I   S   D   S   G   G   N   D   R   L   S
```

FIG. 3G

```
2940                                 2960                                        29
TTCGCGGACTCAAATCTTAAAGATTTGACCTTTGAAAAAGTTAACCACCACCTTATGATC
 F  A  D  S  N  L  K  D  L  T  F  E  K  V  N  H  H  L  M  I
80                                3000                                3020                                30
ACTAATGTGAAAAAAGAAAAAGTAACTATTCAAAACTGGTTCCGTGAAGCCGATTATGCT
 T  N  V  K  K  E  K  V  T  I  Q  N  W  F  R  E  A  D  Y  A
40                                3060                                3080                                31
AAAACTGTGCATAATTATCAAGCAACCGCAGACGAAAAAATTGAAGAAATCATTGGTCGA
 K  T  V  H  N  Y  Q  A  T  A  D  E  K  I  E  E  I  I  G  R
00                                3120                                3140                                31
CAAGGTGAGCGTATTACCTCTAAGCAAATTGATGAGCTGATCGAAAAAGGTAAAGGTAAA
 Q  G  E  R  I  T  S  K  Q  I  D  E  L  I  E  K  G  K  G  K
60                                3180                                3200                                32
ATTGATCAGAGTGAATTGGAGAGAATTGCTGAAAGCAGTGCTTTACTCAAAGAAAGTAAA
 I  D  Q  S  E  L  E  R  I  A  E  S  S  A  L  L  K  E  S  K
20                                3240                                3260                                32
TTTGCTTCAAATAGCTTAAATAAACTTGTTTCATCTGCAGCGCATTTGCCTCTTCAAACG
 F  A  S  N  S  L  N  K  L  V  S  S  A  A  H  L  P  L  Q  T
80                                3300                                3320                                33
ATAACAGAGTGGGCTTGGCGTTCCTACATCATTGTATGAACATACCCAATCTGTACAATT
 I  T  E  W  A  W  R  S  Y  I  I  V
40                                3360                                3380                                34
TGTAAGAGCAGCTTAATATTTTAAATGTTTAGCAACTCTATATTGTTTACGCCATTATGG
                                ------------->          <------
00                                3420                                3440                                34
AGTTGCTATTTTATTTTTTAAAAGGAGATTTCATGGAAGTTAATCATCAAAGCCAATTGA
---------**********
                                          M  E  V  N  H  Q  S  Q  L
60
TCTTGGAT
I  L  D
```

LEUKOTOXIN GENE FROM *PASTEURELLA SUIS*

This is a division of application Ser. No. 07/972,157 filed on Nov. 5, 1992, abandoned.

FIELD OF THE INVENTION

The present invention relates generally to gram-negative bacterium which secrete high molecular weight calcium-dependant cytotoxic proteins (RTX family). More particularly, the invention relates to a new species of gram-negative bacterium, designated *"Pasteurella suis,"* which was isolated from piglets with diarrhea, a gene or gene fragment encoding a novel leukotoxin secreted from *Pasteurella suis*, recombinant DNA sequences and expression systems for directing expression of the gene, a method of using the gene or gene fragment as an immunogen in vaccine formulations and as reagents in diagnostic assays.

BACKGROUND OF THE INVENTION

In the past several years, a number of Gram-negative bacterium have been discovered which secrete high molecular weight (100–110 kDa) calcium-dependent cytotoxic proteins which are immunologically and genetically related to the alpha-hemolysin (HlyA) of *E. coli*. These toxins have been designated the RTX (Repeat of Toxin) family on the basis of a series of glycine/aspartic acid-rich nonapeptide repeats found in the carboxylterminal third of the toxin protein (McWhinney et al., Separable Domains Define Target Cell Specificities of an RTX Hemolysin from *Actinobacillus pleuropneumoniae*, 1992, *J. Bacteriol.*, vol. 174, pp. 291–297). The genetic determinants for the secreted RTX toxins consist of four genes: "A", the structural gene for toxin protein; "C", which is required for "activation" of the toxin prior to secretion; and "B" and "D", which are essential for the process of secretion. The four RTX genes are typically found in a single transcriptional unit, "CABD", and are expressed from a common promoter located upstream of the "C" gene (Felmleel et al., Nucleotide Sequence of an *Escherichia coli* Chromosomal Hemolysin, 1985, *J. Bacteriol.*, vol. 163, pp. 94–105; Highlander et al., Secretion and Expression of *Pasteurella haemolytica* leukotoxin, 1990, *J. Bacteriol.*, vol. 172, pp.2343–2350; and Mackman et al., Genetical and Functional Organization of the *Escherichia coli* Haemolysin Determinant 2001, 1985, *Mol. Gen. Genet.*, vol. 201, pp.282–288). However, in *Actinobacillus pleuropneumoniae* determinants (AppII), the B and D gene pairs are lost during the evolutionary process (Chang et al., "The *Actinobacillus pleuropneumoniae* Hemolysin Determinant: Unlinked AppCA and AppBD Loci Flanked by Pseudogenes", 1991, *J. Bacteriol.*vol. 173, pp. 5151–5158).

A new species of organism has been isolated from pigs with enteritis, which is the basis of this application. The organism is a new member of the RTX family and has been characterized by Oberst et al. DNA-DNA hybridization studies showed that this organism could be distinguished from other organisms such as *Pasteurella haemolytica* (*P. haemolytica*), *Pasteurella multocida* (*P. multocida*), *Escherichia coli, Pseudomonas aeruginosa, Actinobacillus pleuropneumoniae*, and *Salmonella choleraesuis* . The proposed name for this new species of bacterium is *"Pasteurella suis (P. suis)"*. *P. suis* secretes a leukotoxin with similar molecular weight to that of *P. haemolytica* leukotoxin (105 kDa). This leukotoxin is less species specific than that of *P. haemolytica* leukotoxin, because it kills both BL-3 cells and pig leukocytes. The gene or gene fragment encoding the novel leukotoxin secreted from *P. suis* can be used as immunogens in vaccine formulations to immunize pigs against diarrhea and as reagents in diagnostic assays.

SUMMARY OF THE INVENTION

The present invention is directed to a new species of bacterium which has been isolated from piglets with enteritis (diarrhea) and a novel leukotoxin (cytotoxic protein) secreted from the bacterium, as well as the molecularly cloned gene(s) or gene fragment(s) which encode this cytotoxic protein. The leukotoxin (cytotoxic protein) of the invention and related peptides and/or proteins can be used as immunogens in vaccine formulations for pigs against diarrhea.

The leukotoxin (cytotoxic protein) of the present invention can be purified from the bacterium or produced using recombinant DNA techniques in any vector-host system, or synthesized by chemical methods. Accordingly, the invention is also directed to novel DNA sequences and corresponding amino acid sequences and vectors including plasmid DNA, and vital DNA such as human viruses, animal viruses, insect viruses or bacteriophages which can be used to direct the expression of the leukotoxin (cytotoxic protein) and related proteins and/or peptides in appropriate host cells from which the proteins and/or peptides can be purified.

More preferably, the present invention discloses *Pasteurella suis*, a new species of bacterium isolated from piglets with diarrhea, which secretes a 105 kilodaltons (kDa) leukotoxin into the culture media. A series of recombinant phages which produced the leukotoxin when expressed in *E. coli* were identified. Also disclosed is the cloning and sequencing of the novel gene(s) or gene fragment(s), designated pslktC and pslktA (pslktCA) which encode for the leukotoxin (cytotoxic protein) of the invention.

BRIEF DESCRIPTION OF THE DRAWING FIGURES

FIG. 1(*a*) shows a Western blot analysis of culture supernatants from *P. haemolytica, P. multocida* and *P. suis* using cattle anti-leukotoxin serum as the first antibody. *P. haemoytica* strain 629 (lane 1), *P. haemolytica* p1148 (lane 2), *P. multocida p*1059 (lane 3), *P. Suis* strains 6451A, 6749A, 900B, 5943, and 18617 (lane 4 to 8, respectively).

FIG. 1(*b*) shows a Western blot analysis of antigenic proteins expressed from recombinant bacteriophage. Lysates were from *E. coli* LE392 infected with λ-Dash (lane 1), λyfc34 (lane 2), and λyfc35 (lane 3). The truncated protein (λyfc36, lane 4) is indicated by an arrow. Leukotoxin secreted by *P. suis* is shown in lane 5. Prestained molecular markers (Sigma Chemical Company, St. Louis, Mo.) and their apparent molecular weights are shown in kDa.

FIG. 2 shows the restriction map of *P. suis* leukotoxin clones. EcoRI sites derived from the vector flank the inserts of each clone. The locations of the two open reading frames designated pslktC and pslktA are shown (E=EcoRI; P=Pstl; S=SalI; X=XbaI).

FIG. 3 shows the nucleotide sequence of the pslktCA region and the predicted amino acid sequences of the pslktC and pslktA proteins. Promoter-like regions proximal to the pslktC are indicated by the symbol A directly beneath the nucleotide sequence. Potential ribosome binding sequences preceeding pslktC, pslktA and immediately after pslktA are indicated by an underline. A potential rho-independent transcription terminator and polyT track distal pslktA are indicated by <------> and *** , respectively. The three transmembrane segments are doubly underlined within the pslktA amino acid sequence. The glycine-rich repeated sequences are underlined within the pslktA sequence.

FIG. 4 shows a Southern blot analysis of five strains of *P. suis* (lane 1, 6451A; lane 2, 6749A; lane 3, 800B; lane 4, *P. multocida* p1059; lane 5, 6451A and lane 6, 5943).

FIG. 5 shows a Western blot analysis of the culture supernatant of TB1 carrying vector pHG165 (lane 1), pYFC93 (lane 3) and *P. suis*, strain 5943 (lane 2). The first antibody was cattle anti-leukotoxin antibody. The apparent molecular weights of prestained standards are shown in kilodaltons.

DETAILED DESCRIPTION OF THE INVENTION

Figure 1A:
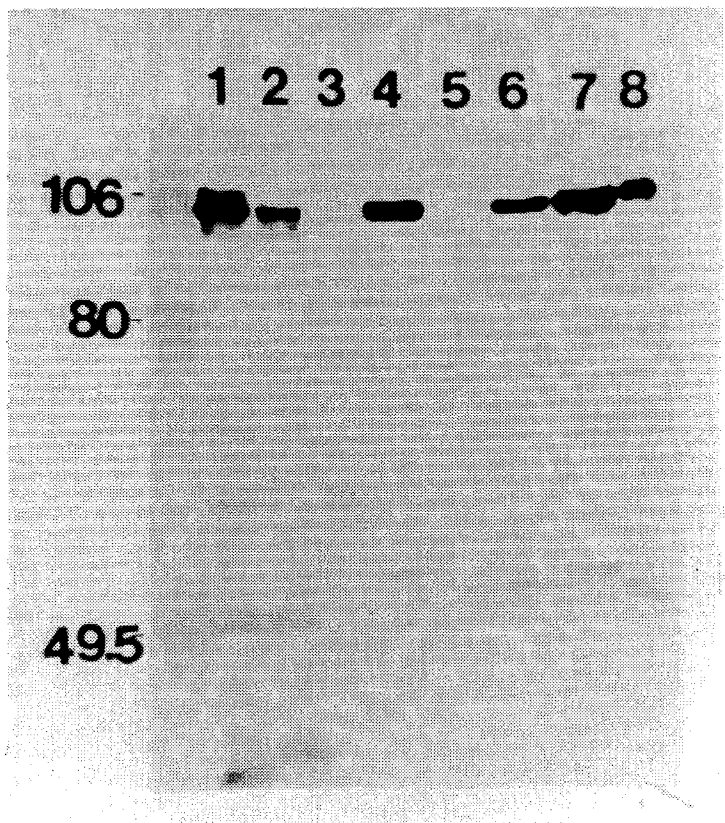

The *Pasteurella suis* strain 5943 and plasmid pYFC93 were deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852, on Mar. 14, 1995, under ATCC Accession No. 55661 and 69760, respectively.

The present invention is directed to a new species of bacterium, designated *Pasteurella suis* (*P. suis*), isolated from pigs with diarrhea. *P. suis* is a gram-negative, nonmotile, beta-hemolytic, pleomorphic, oxidase-positive, urease- and indole- negative organism. *P. suis* secretes a leukotoxin that kills BL-cells as well as fresh pig lymphocytes. This leukotoxin was detected by Western blot analysis by using neutralizing antisera to the *P. haemolytica* leukotoxin. This suggests that *P. suis* is a new member of the RTX family. A *P. suis* genomic library was constructed in the replacement vector λ-dash and screened with a DNA probe derived from pYFC19 which contain lktCA genes of *P. haemolytica*. A series of five overlapping clones which produced a 105 kDa polypeptide when expressed in *E. coli* LE392 were identified. One clone, λyfc36, produced a 78 kDa polypeptide which was a truncated form of the 105 kDa protein (FIG. 1(B), lane 4,). DNA sequence analysis of a 4 kbp region from clone λyfc34 indicated the presence of two open reading frames which were designated pslktC and pslktA. These encode polypeptides of 165 and 934 amino acids, respectively. In addition, there was a potential third open reading frame in the cloned DNA beginning at position 3431 of the sequenced region (FIG. 3). It is believed that this represents the amino-terminal coding region of a putative pslktB gene and that a fourth gene, pslktD, will lie distal to pslktB.

As used herein, "leukotoxin" refers to any cytotoxic protein, mutations and recombinants thereof, secreted from the bacterium *P. suis*. The leukotoxin is encoded by novel gene(s) or gene fragment(s) designated pslktC and pslktA. As used herein, the terms "cytotoxic protein" and/or "exotoxin" are analogous to "leukotoxin".

The apparent molecular weight of the leukotoxin as determined using SDS-PAGE reflects the total molecular weights of the mature (i.e., proteolytically processed) forms, including any post translational modifications. The leukotoxin of the invention can be produced using recombinant DNA methods, by chemical synthesis or can be obtained in substantially pure form from cultures of *P. suis* using methods of isolation and purification. The leukotoxin and/or epitopes thereof can be used as immunogens in various vaccine formulations to protect pigs against *P. suis*, an etiological agent of pig diarrhea. The vaccine formulations can be effective against *P. suis*. More preferably, the leukotoxin of the invention can be combined in a vaccine formulation with gene(s) conferring resistance to other swine diseases such as, for example, with the AppI gene described by Frey et al., Nucleotide Sequence of the Hemolysin I gene from *Actinobacillus pleuropneumoniae*, 1991, *Infect. Immun.*, vol. 59, pp. 3026–2032; the AppII gene described by Chang et al., Cloning and Characterization of a Hemolysin Gene from *Actinobacillus* (Haemophilus) *pleuropneumoniae*, DNA, 1989, vol. 8, pp. 635–647, and/or the AppIII gene described by Chang et al., "Molecular Analysis of a Leukotoxin Gene from *Actinobacillus pleuropneumoniae* serotype 2", Infect. Immun., submitted, which disclosure is hereby incorporated by reference, thereby creating a vaccine which confers resistance to swine against porcine pleuropneumoniae and diarrhea. In addition the leukotoxin of the invention could show cross-protection to *Actinobacillus pleuropneumoniae.*

The present invention also relates to the DNA sequence(s) of the genes pslktC and pslktA which encode for the leukotoxin, as well as the amino acid sequences encoded by the DNA sequences. More particularly, the DNA sequences of the invention encode for two genes, designated pslktC and pslktA. These genes, pslktA and pslktC, collectively pslktCA, encode for the leukotoxin of the invention. The pslktC gene encodes a polypeptide of 165 amino acid residues and the pslktA gene encodes a polypeptide of 934 amino acid residues. The DNA sequence(s) and predicted corresponding amino acid sequences of the present invention are shown in FIG. 3. It is understood that any modifications i.e., insertions, deletions, mutations, recombinants, etc., of the DNA sequence(s) are within the scope of the invention provided that the modified sequence(s) encode for a gene producing a protein, its homologs or a fragment thereof having substantially the same physical, immunological or functional properties as the leukotoxin secreted from *P. suis.*

In accordance with one embodiment of the invention, recombinant DNA techniques are used to insert the DNA sequence(s) of the pslktC and pslktA genes (pslktCA) encoding the leukotoxin into an appropriate expression vector, i.e., a vector which contains the necessary elements for the transcription and translation of the inserted protein-coding sequences. A large number of vector systems known in the art can be used, such as, plasmids, bacteriophage virus or other modified viruses. Suitable vectors include, but are not limited to the following vital vectors such as lambda vector system gt11, gtWES.tB, Charon 4, and plasmid vectors such as pBR322, pBR325, pACYC177, pACYC184, pAR series, pKK223-3, pUC8, pUC9, pUC18, pUC19, pLG339, pR290, pKC37, pKC101 and other similar systems. The DNA sequences are cloned into the vector using standard cloning procedures in the art, as described by Maniatis et al., 1982, Molecular Cloning: A Laboratory Manual, Cold Springs Laboratory, Cold Springs Harbor, N.Y., which reference is hereby incorporated by reference.

The vector system must be compatible with the host cell used. The recombinant vectors can be introduced into the host cells via transformation, transfection or infection using standard techniques in the art. A variety of host cell systems can be used to express the protein-encoding sequence(s). For example, host cell systems include, but are not limited to the following: bacteria transformed with bacteriophage DNA, plasmid DNA or cosmid DNA such as *E. coli* JM103, *E. coli* C600, *E. coli* CO4, *E. coli* DH20 and *E. coli* TB1; microorganisms such as yeast containing yeast vectors; mammalian cell systems infected with virus (vaccinia virus, adenovirus, etc.); insect cell systems infected with virus (baculovirus).

In order to obtain efficient expression of the gene or gene fragments, a promotor must be present in the expression vector, RNA polymerase normally binds to the promotor and initiates transcription of a gene or a group of linked genes and regulatory elements (operon). Promotors vary in their strength, i.e., ability to promote transcription. For the purpose of expressing the cloned gene(s) of the invention, it is desirable to use strong promotors in order to obtain a high level of transcription and, hence, expression of the gene(s). Depending upon the host cell system utilized, any one of a number of suitable promotors can be used. For example, when cloning in *E. coli*, its bacteriophages or plasmids, promotors such as the lac promotor, trp promotor, recA promotor, ribosomal RNA promotor, the $P_R$ and $P_L$ promotors of coliphage lambda and others including but not limited to lacUV5, ompF, bla, lpp and the like, can be used to direct high levels of transcription of adjacent DNA segments. Additionally, a hybrid trp-lacUV5 (tac) promotor or other *E. coli* promotors produced by recombinant DNA or other synthetic DNA techniques can be used to provide for transcription of the inserted gene(s).

Bacterial host cell strains and expression vectors can be chosen which inhibit the action of the promotor unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promotor of lambda can be induced by an increase in temperature in host cells containing a temperature sensitive lambda repressor, e.g., c1857. In this way, greater than 95% of the promotor-directed transcription may be inhibited in uninduced cells. Thus, expression of the genetically engineered cytotoxin protein (leukotoxin) can be controlled. This is important if the protein product of the cloned gene is lethal or detrimental to host cells. In such cases, transformants may be cultured under conditions such that the promotor is not induced, and when the cells reach a suitable density in the growth medium, the promotor can be induced for production of the protein.

One such promotor/operator system is the so-called "tac" or trp-lac promotor/operator system (Russell and Bennett, 1982, *Gene* vol 20, pp.231–243, which disclosure is,hereby incorporated by reference). This hybrid promotor is constructed by combining the −35 b.p. (−35 region) of the trp promotor and the −10 b.p. (−10 region or Pribnow box) of the lac promotor (the sequences of DNA which are the RNA polymerase binding site). In addition to maintaining the strong promotor characteristics of the tryptophan promotor, tac is also controlled by the lac repressor.

When cloning in a eucaryotic host cell, enhancer sequences (e.g., the 72 bp tandem repeat of SV40 DNA or the retroviral long terminal repeats or LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promotor elements (e.g., the polymerase binding site and the Goldberg-Hogness "TATA" box) which must be located immediately 5' to the gene, enhancer sequences have the remarkable ability to function upstream from, within, or downstream from eucaryotic genes. Therefore, the position of the enhancer sequence with respect to the inserted gene is less critical.

Specific initiation signals are also required for efficient gene transcription and translation in procaryotic cell. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes can be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides can be used.

Any of the conventional cloning methods for insertion of DNA fragments into a vector can be used to ligate the promotor and other control elements into specific sites within the vector. Accordingly, *P. suis* genetic sequences containing those regions coding for the cytotoxic protein (leukotoxin) can be ligated into an expression vector at a specific site in relation to the vector promotor and control elements so that when the recombinant DNA molecule is introduced into a host cell the foreign genetic sequence can be expressed (i.e., transcribed and translated) by the host cell.

As previously mentioned, the recombinant DNA molecule can be introduced into appropriate host cells (including but not limited to bacteria, virus, yeast, mammalian cells or the like) by transformation, infection or transfection (depending upon the vector/host cell system). Transformants are selected based upon the expression of one or more appropriate gene markers normally present in the vector, such as ampicillin resistance or tetracycline resistance in pBR322, or thymidine kinase activity in eucaryotic host systems. Expression of such marker genes should indicate that the recombinant DNA molecule is intact and is replicating. Expression vectors may be derived from cloning vectors, which usually contain a marker function. Such cloning vectors may include, but are not limited to the following: SV40 and adenovirus, vaccinia virus vectors, insect viruses such as baculoviruses, yeast vectors, bacteriophage vectors such as lambda gt-WES-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col El, pSC101, pBR313, pML21, RSF2124, pCR1, RP4, pBR328 and the like.

In the particular embodiment in the examples of the present invention, an *E. coli* plasmid system was chosen as the expression vector. The invention, however, is not limited to the use of such *E. coli* expression vector. Furthermore, genetic engineering techniques could also be used to further characterize and/or adapt the cloned gene. For example, site directed mutagenesis of the gene encoding the leukotoxin could be used to identify regions of the protein responsible for generation of protective antibody responses. It could also be used to modify the protein in regions outside the protective domains, for example, to increase the solubility of the protein to allow easier purification.

The expression vectors containing the foreign gene inserts (e.g., DNA encoding the leukotoxin) can be identified by three approaches: (1) DNA-DNA hybridization using probes comprising sequences that are homologous to the leukotoxin gene(s); (2) presence or absence of "marker" gene function and (3) expression of inserted sequences based on the physical, immunological or functional properties of the leukotoxin. Once a recombinant which expresses the leukotoxin is identified, the gene product should be analyzed. Immunological analysis is especially important because the ultimate goal is to use the leukotoxin or recombinant expression systems that express the leukotoxin in vaccine formulations and/or as antigens in diagnostic immunoassays. Once the leukotoxin is identified, it is cultured under conditions which facilitate growth of the cells and expression of the leukotoxin as will be apparent to one skilled in the art, then isolated and purified by standard methods including chromatography (e.g., ion exchange, affinity, and sizing column chromatography), centrifugation, differental solubility, or by any other standard techniques for the purification of proteins. In addition, since the amino acid sequence is known from the DNA sequence of the invention, the protein can be synthesized by chemical methods according to the procedure of Hunkapiller et al., 1984, *Nature*, vol. 310, pp. 105–111, which disclosure is hereby incorporated by reference.

In another embodiment of the invention, proteins or polypeptide fragments related to the leukotoxin of the invention can be used as immunogens in a vaccine formulation to protect against diarrhea and other disease symptoms of *P, suis*. Vaccines comprise solely the relevant immunogenic material necessary to immunize a host. Vaccines made from genetically engineered immunogens, chemically synthesized immunogens and/or immunogens comprising authentic substantially pure leukotoxin, which are capable of eliciting a protective immune response are particularly advantageous because there is no risk of infection of the recipients. Thus, the leukotoxin, related proteins or fragments thereof can be purified from recombinants that express the leukotoxin epitopes. Such recombinants include any of the previously described bacterial transformants, yeast transformants, or cultured cells infected with recombinant viruses that express the leukotoxin toxin epitopes.

Whether the immunogen is purified from recombinants or chemically synthesized, the final product is adjusted to an appropriate concentration and formulated with any suitable vaccine adjuvant. Suitable adjuvants include, but are not limited to: surface active substances, e.g., hexadecylamine, octadecylamine, octadecyl amino acid esters, lysolecithin, dimethyl-dioctadecylammonium bromide, N, N-dicoctadecyl-N-Nbis (2-hydroxyethyl-propane diamine), methoxyhexadecylglycerol; polyamines, e.g., pyran, dextransulfate, poly IC, polyacrylic acid; peptides, e.g., muramyl dipeptide, dimethylglycine, tuftsin; oil emulsions; and mineral gels, e.g., aluminum hydroxide, aluminum phosphate, etc. The immunogen can also be incorporated into liposomes, or conjugated to polysaccharides and/or other polymers for use in a vaccine formulation.

In another aspect, the vaccine formulation can comprise live recombinant viral vaccine or an inactivated recombinant vital vaccine which is used to protect against diarrhea in pigs and other disease symptoms of *P. suis*. In addition, multivalent vaccines can be prepared from a single or a few infectious recombinant viruses, proteins or polypeptides that express epitopes of organisms that cause disease in addition to the epitopes of *P. suis*. For example, a vaccine can be engineered to include coding sequences for other epitopes, or a mixture of vaccinia or viruses each expressing a different gene encoding for different epitopes which can confer resistance to other diseases which affect swine. Many methods can be used to introduce the vaccine formulations into the animal. For example, intradermal, intramuscular, intraperitoneal, intravenous, subcutaneous and intranasal routes of administration cab be used.

Instead of actively immunizing with vital or subunit vaccines, it is possible to confer short-term protection to the host by administration of pre-formed antibody against an epitope of *P. suis*. Thus, the vaccine formulations can be used to produce antibodies for use in passive immunotherapy.

Another embodiment of the invention is to provide reagents for use in diagnostic assays for the detection of *P. suis* in various fluids of animals suspected of such infection. For example, the proteins and peptides of the invention can be used in any immunoassay system known in the art including, RIA, ELISA assays, "sandwich" assays, precipitation reactions, gel diffusion precipitation reactions, agglutination assays, fluorescent immunoassays, etc. In another aspect, the DNA sequences of the genes encoding the leukotoxin can be used in nucleic acid hybridization assays.

The following examples are provided to further illustrate the present invention.

EXAMPLE I

Materials and Methods

1. Bacterial Strains, Plasmids, and Growth Conditions:

*P. haemolytica* 629 and p1148 (a streptomycin-dependent mutant) were previously described by Chang et al., "Identification and Characterization of the *Pasteurella haemolytica*", 1987, *Infect. Immun.*, vol 55, pp. 2348–2354; and Chengappa et al., "Improved Method for Obtaining Streptomycin-Dependent Mutants from *Pasteurella multocida* and *Pasteurella haemolytica*, using N-methyl-N'nitrosoquanidine", 1987, *Am. J. Vet. Res.*, vol 40, pp. 449–450, respectively, which disclosures are hereby incorporated by reference. *P. suis* 6451A, 6749A, 900B, 5943, 18617 are described by Oberst et al., *P. multocida* p1059 was isolated from a cow that died of pneumonia as described by Chengappa et al., "Improved Method for Obtaining Streptomycin-Dependent Mutants from *Pasteurella multocida* and *Pasteurella haemolytica*, using N-methyl-N'nitrosoquanidine", 1987, *Am. J. Vet. Res.*, vol 40, pp. 449–450. All Pasteurella strains were grown in brain heart infusion broth. All *E. coli* strains (JM101, supE thi Δ(lacproAB) F' [traD36 proAB+ lacIq lacZΔ1M15]; TB1, ara Δ(lacproAB) rpsL φ80dlacZΔM15 hsdR17 ($r^-m^+$); LE392, hsdR514 ($r^-m^+$) supE44 supF58 lacY1 galK2 galT22 metB1 trpR55; P2392, a P2 lysogen of LE392) were cultured in Luria broth according to Miller, J. H., "Experiments in Molecular Genetics", 1972, p. 433, Cold Spring Harbor Laboratory, Cold Spring Harbor, N.Y., which disclosure is hereby incorporated by reference, and containing the appropriate antibiotics when necessary. The vectors Lambda-Dash, M13mp18, M13mp19, and pHGI65 were as previously described by Chang et al., "Cloning and Characterization of a Hemolysin Gene from *Actinobacillus* (Haemophilus) *pleuropneumoniae*", 1989, *DNA*, vol. 8, pp. 635–647; and Messing, J., "New M13 Vectors for Cloning", 1983, *Methods Enzymol.*, vol. 101, pp. 20–78, which disclosures are hereby incorporated by reference. The intact pslktCA from λyfc34 were subcloned into pHG165 as an EcoRI fragment to form pYFC93.

2. SDS-PAGE and Western blotting:

SDS-PAGE and Western blotting were performed as described by Chang et al., "Identification and Characterization of the *Pasteurella haemolytica*", 1987, *Infect Immun*, vol. 55, pp. 2348–2354; and Chang et al., "Cloning and Characterization of a Hemolysin Gene from *Actinobacillus* (Haemophilus) *pleuropneumoniae*", 1989, *DNA*, vol. 8, pp. 635–647, which disclosures are hereby incorporated by reference, using culture supernatants (5 ml) concentrated by chloroform/methanol/water system as described by Welch et al., "Transcription Organization of the *Escherichia coli* Hemolysin Genes", 1988, *J. Bacteriol*, vol. 170, pp. 1622–1630, which disclosure is hereby incorporated by reference, and resuspended in 150 μm of sample buffer. After boiling for 2 minutes, samples (15 μl) were subjected to SDS-PAGE. Immunoreactive proteins were visualized using cattle anti-leukotoxin and an anti-cattle IgG second antibody conjugated to alkaline phosphatase as described by Chang et al., "Identification and Characterization of the *Pasteurella haemolytica*", 1987, *Infect Immun*, vol. 55, pp. 2348–2354, which disclosure is hereby incorporated by reference.

3. Construction of a Genomic Bank of *P. suis* DNA in λ-dash:

*P. suis* chromosomal DNA from strain 5943 was isolated as described by Chang et al., "Cloning and Characterization of a Hemolysin Gene from *Actinobacillus* (Haemophilus) *pleuropneumoniae*", 1989, DNA, vol. 8, pp. 635–647; and Silhavy et al., "Experiments in Gene Fusions", 1984, p. 89–90, Cold Spring Harbor Laboratory, Cold Spring Harbor, N.Y., which disclosures are hereby incorporated by reference, and partially digested with Sau3A. The digested DNA was fractionated by sedimentation through a 10–40% sucrose gradient as described by Chang et al., "Identification and Characterization of the *Pasteurella haemolytica*", 1987, *Infect Immun*, vol. 55, pp. 2348–2354; and Chang et al., "Cloning and Characterization of a Hemolysin Gene from *Actinobacillus* (Haemophilus) *pleuropneumoniae*", 1989, *DNA*, vol. 8, pp. 635–647, which disclosures are hereby incorporated by reference, and fractions containing 9- to 20-kbp fragments, as judged by agarose gel/electrophoresis, were pooled and concentrated by alcohol precipitation to a final concentration of 100 pg/ml. λ-dash was cleaved with BamHI and treated with alkaline phosphatase to remove terminal phosphatase. After phenol extraction and concentration by ethanol precipitation, the vector DNA was mixed with size-selected *P. suis* DNA at a molar ratio of 1:4 and treated with T4 DNA ligase for 16 hours at 150° C. The ligated DNA mixture was packaged into λparticles using the commercially available in vitro packaging kit GIGAPACK PLUS (Stratagene, La Jolla, Calif.). The phage titers were determined and amplified on P2392.

4. Phage Library Screening for *P. suis* Leukotoxin Gene:

The bacteriophage library was screened by hybridization using a probe containing the lktCA genes from *P. haemolytica*. A DNA fragment from pYFC19 as described by Chang et al., "Identification and Characterization of the *Pasteurella haemolytica*", 1987, *Infect Immun*, vol. 55, pp. 2348–2354, which disclosure is hereby incorporated by reference, containing the lktCA genes was labeled with [$^{32}$P]dATP by nick-translation. Filters were hybridized in 45% formamide, 5×SSC (20×SSC containing 175.3 gm of NaCl and 88.2 gm of sodium citrate per liter, pH 7.0), 5×Denhardt's solution, and 100 μg/ml sheared calf thymus DNA for 12 hours at 37° C. Filters were; then washed twice with 2×SSC-0.1% SDS and twice with 0.2% SSC-0.1% SDS at room temperature. The final wash was with 0.16% SSC-0.1% SDS at 37° C. Plaques which gave positive signals were picked, rescreened, and amplified on P2392.

5. DNA Sequencing and Analysis:

DNA sequencing was performed by the dideoxy chain termination method as described by Sanger et al., "DNA Sequencing with Chain-Termination Inhibitors", 1977, *Proc. Natl. Acad. Sci.*, vol. 74, pp. 5463–5467, which disclosure is hereby incorporated by reference. Regions from the *P. suis* insert in bacteriophage clone λyfc34 were subcloned into M13mp18 or M13mp19 and single stranded phage DNA was prepared according to the procedures of Messing, J., "New M13 Vectors for Cloning", 1983, *Methods Enzymol.*, vol. 101, pp. 20–78, which disclosure is hereby incorporated by reference. The sequencing reactions utilized [$^{35}$S]dATP, T7 DNA polymerase, and the commercially available SEQUENASE KIT (United States Biochemicals, Cleveland, Ohio). Certain regions of the DNA insert were sequenced directly from the recombinant bacteriophage. In these cases, 1–2 μpg of λyfc34 DNA was mixed with 100 ng of an oligonucleotide primer (prepared by the Analytical and Synthetic Facility, Cornell University, Ithaca, N.Y.) in a total volume of 12 μl, boiled for 5 minutes, and then cooled rapidly on ice. The sequencing reactions were performed with reagents supplied with the SEQUENASE KIT (United States Biochemicals, Cleveland, Ohio) according to the manufacturer's instructions. DNA sequence analysis was performed on a VAX computer using the Genetics Computer Group program package (University of Wisconsin, Madison, Wis.). The amino acid sequence alignment was carried out with the GAP and LINEUP programs (Genetics Computer Group, University of Wisconsin, Madison, Wis.) and similarity was calculated according to the method of Pearson and Lipman, "Improved Tools for Biological Sequence Comparison", 1988, *Proc. Natl. Aced. Sci.*, vol. 85, pp. 2444–2448, which disclosure is hereby incorporated by reference.

6. Southern Blotting Analysis:

*P. suis* genomic DNA from different isolates were digested with PstI, electrophoresed through a 0.7% agarose gel, transferred to nitrocellulose membrane and probed with XbaI-SalI fragment containing three 120 bp partial pslktCA genes isolated from λyfc34. Filter treatment and hybridization procedures are as described in (4) above.

7. Cytotoxic Activity Assay:

Pig leukocytes were prepared as described by Buschmann et al., "A Study of Porcine Lymphocytes Populations: Separation of Porcine Lymphocyte Subpopulations", 1980, *Vet. Immun. Immunopath.*, vol. 1, pp. 215–224, which disclosure is hereby incorporated by reference. The cytotoxic activity of *P. suis* leukotoxin to freshly prepared pig leukocytes and BL-3 cells were assayed as described by Chang et al., "Identification and Characterization of the *Pasteurella haemolytica*", 1987, *Infect Immun*, vol. 55, pp. 2348–2354, which disclosure is hereby incorporated by reference. Both the BL-3 cells and fresh pig leukocytes undergo similar characteristic morphological changes upon exposure to the active leukotoxin from *P. suis* and also similar to that of changes by *P. haemolytica* leukotoxin (Chang et al., "Identification and Characterization of the *Pasteurella haemolytica*", 1987, *Infect Immun*, vol. 55, pp. 2348–2354, which disclosure is hereby incorporated by reference).

EXAMPLE II

Western Blotting Analysis

To determine whether *P. suis* also secreted the leukotoxin, the culture supernatants from two *P. haemolytica* strains, *P. multocida* and five strains of *P. suis* were analyzed by Western blot, using cattle antiserum raised against *P. haemolytica* leukotoxin. With reference to FIG. 1(A), a cross-reacting polypeptide species with 105 kDa was identified. Thus, the *P. suis* leukotoxin, which was designated psLkt, is immunologically related to *P. haemolytica* RTX toxin.

EXAMPLE III

Cloning of The pslkt Locus

Figure 1B:
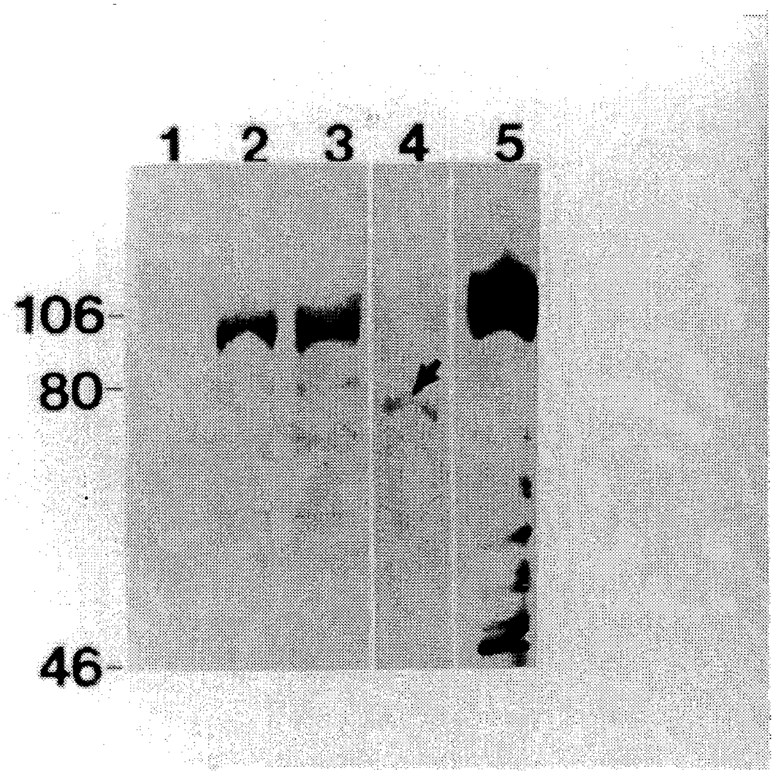
Figure 2:
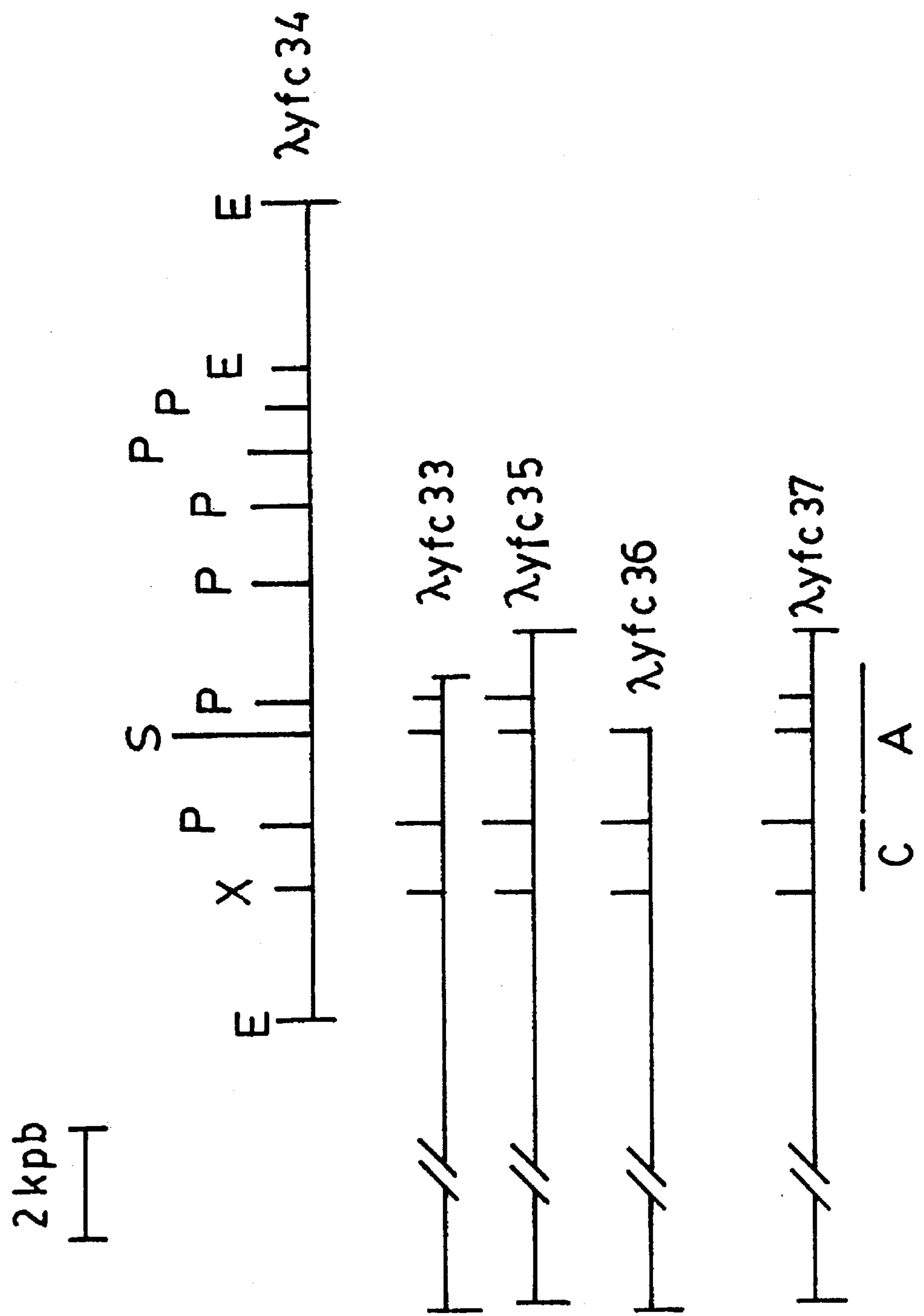
Figure 4:
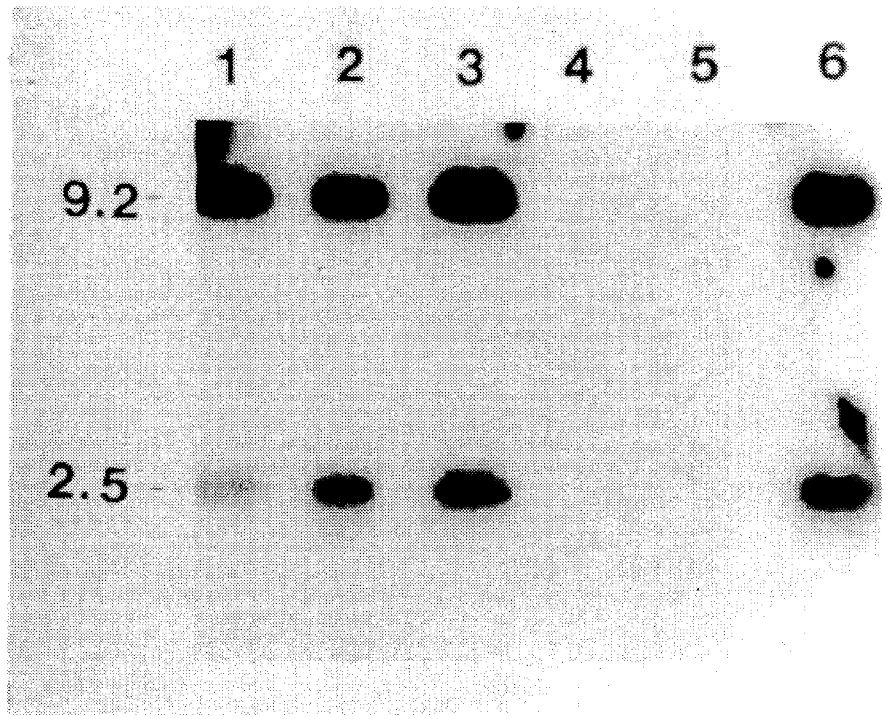

*P. suis* genomic library constructed in the phage vector λ-dash was screened with a DNA probe derived from pYFC19, a plasmid carrying the lktCA locus as described by Chang et al., "Identification and Characterization of *Pasteurella haemolytica*", 1987, *Infect Immun*, vol. 55, pp. 2348–2354, which disclosure is hereby incorporated by reference. With reference to FIG. 2, five clones were isolated which overlapped each other. Except λ- yfc36, all other clones expressed about a 105 kDa polypeptide detected by Western blot with the anti-leukotoxin antibody as shown in FIG. 1(B). With reference to FIG. 4, lane 4, λyfc36 produced a truncated polypeptide of about 70 kDa . The fact that this clone expressed a truncated toxin provided a location and orientation for the putative leukotoxin locus within the cloned DNA. Southern blot analysis using an XbaI-PstI fragment, which maps to the leukotoxin determinants as judged by DNA sequencing, showed (FIG. 4) that no detectable rearrangement occurred during the cloning procedure. Despite the fact that all four clones were identified which produced the full length of leukotoxin, no cytotoxic activity could be detected in any of the phage lysates (data not shown).

EXAMPLE IV

DNA Sequence of pslktCA Genes

A 4 kbp region indicated by the truncated clone (FIG. 3) was subjected to DNA sequence analysis. As in the case of the RTX loci, there is a small open reading frame (ORF) preceding the toxin open reading frame, presumably encoding the pslktC gene (FIG. 3). The pslktCA genes are more closely related to the lktCA from *P. haemolytica* than to other RTX gene family. Table 1 summarizes the similarities between pslktCA and the other RTX CA genes for which sequence information is available.

TABLE 1

| | pslktC gene | pslktA gene |
|---|---|---|
| 1. Homology to the leukotoxin locus of *P. haemolytica* (lkt) | | |
| Nucleotide sequence | 86.7% | 75.7% |
| Amino acid sequence | 86.0% | 86.8% |
| 2. Homology to the hemolysin locus of *A. pleuropneumoniae* (hlyI) | | |
| Nucleotide sequence[a] | 68.6% | 58.8% |
| Amino acid sequence[b] | 75.5% | 65.4% |
| 3. Homology to the hemolysin locus of *A. pleuropneumoniae* (AppII) | | |
| Nucleotide sequence | 63.3% | 66.8% |
| Amino acid sequence | 69.7% | 76.7% |
| 4. Homology to the hemolysin locus of *E. coli* (hly) | | |
| Nucleotide sequence | 58.1% | 60.3% |
| Amino acid sequence | 66.0% | 66.2% |
| 5. Homology to the hemolysin locus of *A. actinomycetemcomitans* (aalkt) | | |
| Nucleotide sequence | 62.7% | 58.4% |
| Amino acid sequence | 65.2% | 64.2% |

The pslktCA sequence was examined for *E. coli* promoter-like sequences using the homology score method as described by Mulligan et al., *Escherichia coli* promoter sequences predict in vitro RNA polymerase selectivity, 1984, *Nucl. Acid Res.*, vol. 12, pp. 789–800, which disclosure is hereby incorporated by reference. There were two sequences, TAATCT and TAAAAT, similar to the TATAAT consensus promoter sequence (−10 region) and one sequence, TTGATT, similar to the consensus RNA polymerase-binding site (−35 region) proximal to pslktC (FIG. 3). Upstream of the start codon of pslktC, there is a potential ribosome binding site (FIG. 3). A ribosome binding site lies proximal to the pslktA (FIG. 3). A sequence very similar to the rho-independent transcriptional terminator of *E. coli* downstream from pslktA was also observed (FIG. 3).

The hydrophobicity of the deduced amino acids of pslktA and its potential membrane-spanning regions was analyzed according to the method of Klein et al., "The Detection and Classification of Membrane-Spanning Proteins", 1985, *Biochim. Biopbys. Acta*, vol. 815, pp. 468–476, which disclosure is hereby incorporated by reference. The analysis identified three potential transmembrane regions on pslktA between amino acid 154 to 170, 312 to 333 and 393 to 414 (FIG. 3).

EXAMPLE V

Southern Blotting Analysis

To demonstrate the distribution of the pslktCA genes among different field isolates of *P. suis*, the 3,120 bp XbaI-SalI fragment from λyfc34 was purified, nick translated with ($^{32}$P)dATP, and used as a hybridization probe on genomic DNA of *P. suis* field isolates in Southern blots. Except for *P. suis* strain 6551A, all other strains contain two unique signals, 2.5 and 9.2 kbp, respectively, as shown in FIG. 4.

EXAMPLE VI

Expression Of Cytotoxic Activity in *E. coli*

Figure 5:
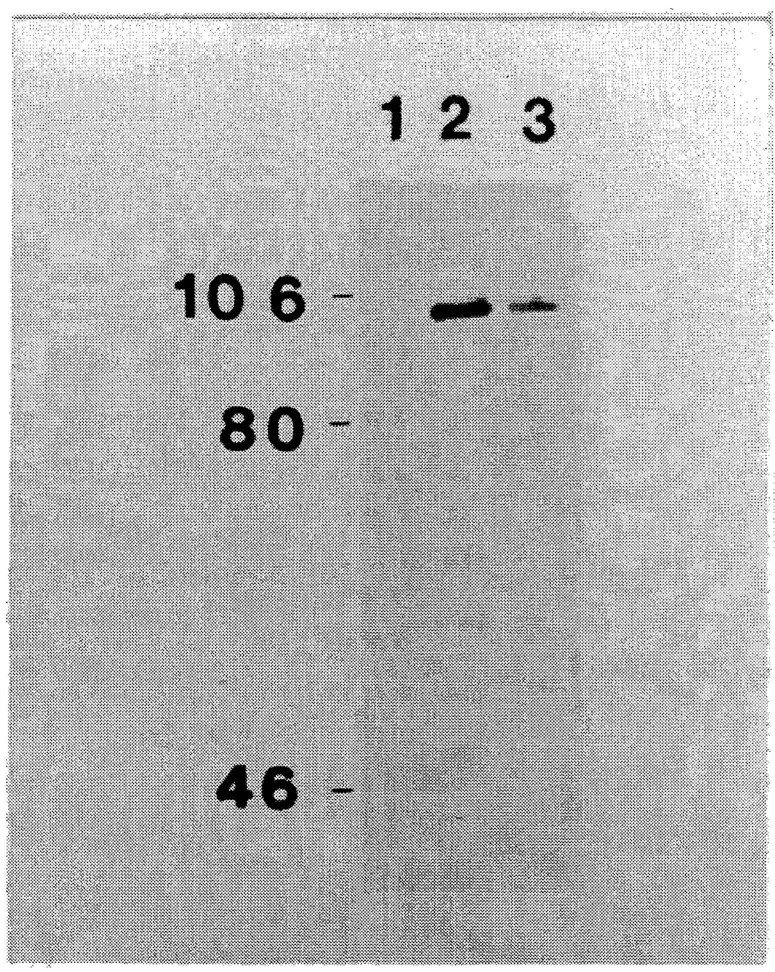

The pslktCA region from λyfc34 (FIG. 2) was subcloned into vector pHG165 according to the method of Stewart et al., "A pBR322 Copy Number Derivation of pUC8 for Cloning and Expression", 1986, *Plasmid*, vol. 15, pp. 172–186, which disclosure is hereby incorporated by reference, as an EcoRI fragment yielding plasmid, pYFC93 (pslktCA). This clone is likely to be expressed from the *P. suis* promoter and to contain pslktBD genes, because toxin was detected in the media, as shown in FIG. 5. With reference to Table 3, in the culture supernatant of *P. suis* strain 5943, there was detected 156 and 142 toxin units per ml using BL-3 cells and pig lymphocytes, respectively. Using the culture supernatant of *E. coli* harboring pYFC93, there was detected 96 toxin units per ml by using either BL-3 cells or pig lymphocytes (Table 3). However, using culture supernatant from *E. coli* harboring vector pHG165, no toxin activity was detected (Table 3). The leukotoxic activity from *E. coli* harboring pYFC93 could be neutralized by cattle anti-*P. haemolytica* leukotoxin antibody as was the case with the leukotoxin from *P. suis* (data not shown).

RESULTS

Leukotoxin activity in lysates prepared by infecting *E. coli* with any of the bacteriophage clones was not detected. This was similar to the *A. pleuropneumoniae* hemolysin gene clones as described by Chang et al., "Cloning and Characterization of a Hemolysin Gene from *Actinobacillus* (Haemophilus) *pleuropneumoniae*", 1989, *DNA*, vol. 8, pp. 635–647, which disclosure is hereby incorporated by reference. When the pslktCA genes were subcloned into a multicopy plasmid vector, the recombinant plasmid expressed the 105 kDa protein (FIG. 5) with leukotoxin activity (Table. 3). Since the leukotoxin was secreted into media, it is believed that this clone contains the complete gene cluster, pslktCABD.

The predicted pslktC and pslktA proteins have 86.6% and 86.8% similarity with the corresponding lktC and lktA proteins from *P. haemolytica* leukotoxin determinant. The pslktA cytotoxin, as was the case with the other RTX toxins, does not exhibit classic signal sequences at its amino terminus. Instead, the predicted amino terminus is rich in serine, threonine, and lysine (13 of the first 39 residues) and has the capability of forming a positive charged, amphophilic alpha-helix as does the amino termini of other RTX toxins (Highlander et al., "DNA Sequence of the *Pasteurella haemolytica* Leukotoxin Gene Cluster", 1989, *DNA*, vol. 8, pp. 15–29, which disclosure is hereby incorporated by reference). There are three transmembrane domains in the N-terminal part of the protein (FIG. 3). These structural features have been reported to facilitate the interaction of this class of lytic toxins with target membranes. There are eight glycine-rich repeats in the second half of the pslktA (Table 2.). The glycine-rich repeats have been reported to be responsible for cell-binding. With reference to Table 2, amino acid residues within the glycine-rich repeated domains of AppIA (HlyIA), AppIIA (AppA), AppIIIA, lktA, aalktA, and HlyA are shown. pslktA (present invention) and lktA (Highlander et al., "DNA Sequence of the *Pasteurella haemolytica* Leukotoxin Gene Cluster", 1989, *DNA*, vol. 8, pp. 15–29; Chang et al., "Identification and Characterization of the *Pasteurella haemolytica*", 1987, *Infect Immun*, vol. 55, pp. 2348–2354; and Lo et al., "Nucleotide Sequence of the Leukotoxin Genes of *Pasteurella haemolytica* Al" 1987, *Infect. Immun.*, vol. 55, pp. 1987–1996, which disclosures are hereby incorporated by reference) contain eight glycine-rich repeats, aalktA (Kraig et al., "Nucleotide Sequence of the Leukotoxin Gene From *Actinobacillus actinomycetemcomintans*: Homology to the Alpha-Hemolysisn/Leukotoxin Gene Family", 1990, *Infect. Immun.*, vol. 58, pp. 920–929; and Lally et al., "Analysis of the *Actinobacillus actinomycetemcomintans* Leukotoxin Gene", *J. Biol. Chem.*, vol. 264, pp. 15451–15456, which disclosures are hereby incorporated by reference) fourteen and AppIIIA (Chang et al. thirteen. *P. suis* leukotoxin is less specific than the P. haemolytica leukotoxin since the former kills both cattle and pigs leukocytes.

TABLE 2

| | Sequence Domain (Seq. ID NOS. 3–80) | | | | | | |
|---|---|---|---|---|---|---|---|
| | pslktA | AppIIA (AppA) | lkta | aalktA | AppIIIA | HlyIA (AppIA) | HlyA |
| 1 | IIGTSRNDI | LIGTTRADK | IIGTSHNDI | IIGSTLRDK | EIGSNQRDE | IIGSNRKDK | IIGSQFNDI |
| 2 | FKGSKFDDA | FFGSKAFAD | IFKGLFMDA | FYGSKFNDV | FKGSKFRDI | FFGSRFTDI | FKGSQFDDV |
| 3 | FHGGDGVDN | FHGADGDDH | FNGGDGVDA | FHGHDGDDL | FHGADGDDL | FHGAKGDDE | FHGGNGVDT |
| 4 | IDGNAGNDR | IEGNDGNDR | IYGNDGNDR | IYGYDGDDR | LNGNDGDDI | LYGNDGNDI | IDGNDGDDH |
| 5 | LFGGKGFDI | LYGDKGNDT | LFGGKGDDI | LYGDNGNDE | LYGDKGNDE | LYGGDGNDI | LRGGAGDDV |
| 6 | IDGGDGDDF | LSGGNGDDQ | LDGGNGDDF | IHGCQGNDK | LRGDNGNDQ | IHGGDGNDH | IDGGNGNNF |
| 7 | IDGGQGDDI | LYGGDGNDK | IDGGKGNDL | LYGGAGNDR | LYGGEGDDK | LVGGNGNDR | LVGGTGNDI |
| 8 | LHGGKGNDI | LIGGAGGNY | LHGGKGDDI | LFGEYGNNY | LLGGNGNNY | LIGGKGNNF | ISGGKDNDI |
| 9 | | | LDGGEGDDH | LSGGDGNDE | LNGGDGDDE | LNGGDGDDE | |
| 10 | | | LEGGNGSDI | LRGGKGDDK | LLGGAGNDI | LSGGKGNDK | |
| 11 | | | LRGGSGNDK | LYGSSGSDL | LYGSDGTNL | LYGSEGADL | |
| 12 | | | LFGNQGDDL | LDGGEGNDY | FDGGVGNDK | LDGGEGNDL | |
| 13 | | | LDGGEGDDQ | LEGGDGSDF | IYGGLGKDI | LKGGYGNDI | |
| 14 | | | LAGGEGNDF | | | | |

In summary, the DNA sequencing results have shown that pslktA is a member of RTX family. The level of similarity between lktA and pslktA suggests they diverged only recently. In *P. haemolytica*, almost all the strains contain this leukotoxin determinant as described by Chang et al., In contrast, not all the strains of *P. suis* carry the leukotoxin determinants as shown herein. Whether the P. suis leukotoxin gene cluster is derived from *P. haemolytica* is unknown. The *A. pleuropneumoniae* serotype 7 hemolysin determinants are flanked by identical direct repeats. The presence of these repeats allows for participation of this DNA region in homologous recombination. Examination of the flanking regions of the *P. suis* toxin determinants for the presence of identical repeats will enable us to determine if the *P. suis* toxin determinants could be mobile using a similar mechanism.

The invention has been described in detail with particular reference to preferred embodiments thereof, but it will be understood that variations and modifications can be effected within the spirit and scope of the invention.

TABLE 3

| | cytotoxic activity | |
|---|---|---|
| Toxin | BL-3 cells | Pig lymphocytes |
| Culture supernatant[a] | 156 U[b] | 142 U |
| pYFC93c | 96 U | 96 U |
| pHG165c | 0 U | 0 U |

a. Assay performed with a late log phase supernatant from a culture of *P. suis* strain 5943 grown in brain heart infusion broth.

b. One unit of toxin activity is defined as the minimal amount of toxin, as determined by serial dilution, required to produce the morphological change in π95% of the input BL-3 cells or pig lymphocytes.

c. Assay performed with early stationary phase supernatant from the *E. coli* host, TB1, harboring the indicated plasmid grown in LB with ampicillin (50 μg/ml).

We claim:

1. An isolated DNA molecule encoding a pslktA gene product of *Pasteurella suis.*

2. The DNA molecule of claim 1 wherein said DNA includes a nucleotide sequence as shown in SEQ ID No: 79.

3. A vector comprising the DNA of claim 1.

4. A cell comprising the vector of claim 3.

5. The vector of claim 3, further comprising the pslkt promoter.

6. A bacterial cell comprising the vector of claim 5.

7. A method of producing the pslktA gene product of *Pasteurella suis*, said method comprising treating the cell according to claim 6 so that the pslktA gene product is expressed, recovering said gene product from the host, and purifying the product so recovered.

8. An expression vector comprising the DNA molecule of claim 1 and suitable regulatory elements positioned relative to the DNA molecule so as to effect expression of the pslktA gene product in a host cell.

9. The expression vector of claim 8 wherein the vector comprises a plasmid.

10. A cell comprising the expression vector of claim 8.

11. A method of producing a pslktA gene product, said method comprising treating the cell according to claim 10 so that the DNA directs expression of the pslktA gene product and the cell expresses the pslktA gene product and recovering from the cell the pslktA gene product so produced.

12. A bacterial cell comprising the expression vector of claim 8.

13. The bacterial cell of claim 12 wherein the bacterial cell is *Escherichia coli.*

14. A method of producing a pslktA gene product, said method comprising treating the bacterial cell according to claim 12 so that the DNA directs expression of the pslktA gene product and the cell expresses the pslktA gene product and recovering from the cell the pslktA gene product so produced.

15. An isolated DNA molecule encoding a pslktC gene product of *Pasteurella suis.*

16. The DNA molecule of claim 15 wherein said DNA includes a nucleotide sequence as shown in SEQ ID NO: 81.

17. An isolated DNA molecule encoding a pslktB gene product of *Pasteurella suis.*

18. The DNA molecule of claim 17 wherein said DNA includes a 5' nucleotide sequence as shown in SEQ ID NO: 83.

19. An isolated DNA molecule encoding multiple genes of an RTX toxin from the bacterium *Pasteurella suis*, wherein said multiple genes include the pslktC and pslktA genes of *P. suis.*

20. The DNA molecule of claim 19 wherein the DNA molecule includes a nucleotide sequence as shown in SEQ ID NO: 1.

21. A vector comprising the DNA of claim 19.

22. A cell comprising the vector of claim 21.

23. The vector of claim 21, further comprising the pslkt promoter.

24. A bacterial cell comprising the vector of claim 23.

25. A method of producing an RTX toxin, said method comprising treating the cell according to claim 24 so that the cell expresses the toxin and recovering from the cell the toxin so produced.

26. An expression vector comprising the DNA molecule of claim 19 and suitable regulatory elements positioned relative to the DNA molecule so as to effect expression of the RTX toxin in a host cell.

27. The expression vector of claim 26 wherein the vector comprises a plasmid.

28. The expression vector of claim 27 wherein the plasmid is designated pYFC93.

29. A cell comprising the expression vector of claim 26.

30. A method of producing an RTX toxin, said method comprising treating the cell according to claim 29 so that the DNA directs expression of the RTX toxin and the cell expresses the RTX toxin and recovering from the cell the RTX toxin so produced.

31. A bacterial cell comprising the expression vector of claim 26.

32. The bacterial cell of claim 31 wherein the bacterial cell is *Escherichia coli.*

33. A method of producing an RTX toxin, said method comprising treating the bacterial cell according to claim 31 so that the DNA directs expression of the RTX toxin and the cell expresses the RTX toxin and recovering from the cell the RTX toxin so produced.

34. An isolated DNA molecule encoding an amino acid sequence as shown in SEQ ID NO: 80.

35. An isolated DNA molecule encoding an amino acid sequence as shown in SEQ ID NO: 82.

36. An isolated DNA molecule encoding an amino acid sequence having an amino terminal sequence as shown in SEQ ID NO: 84.

* * * * *

SEQUENCE LISTING ( 1 ) GENERAL INFORMATION:

( i i i ) NUMBER OF SEQUENCES: 84

( 2 ) INFORMATION FOR SEQ ID NO:1:

( i ) SEQUENCE CHARACTERISTICS:
( A ) LENGTH: 3848 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:1:

```
GGCAGCATTA ATCCTGGAGG CTTAAACTTA AAATTAAGTG GTCTGATTCT TGCAAAATTT     60
GCACAAATCA GACCGCTGTA TTTTATTTAG CACTCATCTC TTTATTGTAA AATTTTATCC    120
TTACAAAACG ATACCTATCT CTTAAACTTT CTTAAATAAA ATGAAAAGCA AATATTACAT    180
TAATTTTACA ATGTAATTAT TTTGTTTATT TTTCGGCATT TGTGTAACTT TAAAGTATTT    240
TATTTTGCAA TTAATTTACA TGAAAGGCAA AAAACACAAT TAAAACAATT AAAACAATAA    300
AAAATCCTGT GGTAAGATCA GTTGATTAAT ATATTATGCT AAAATTTTGA TTCTAATCTA    360
GAATCATTAT CGAGTGTGAA TTATGAATCA ACATTACTTT AATCTATTGG GAAATATTAC    420
TTGGTTATGG ATGAACTCAC CTCTTCATAG AGAGTGGAGC TGTGAGCTAT TGGCACGCAA    480
TGTGATTCCG GCAATTGAAA ATCAACAATA TATGCTACTT ATTGATAATG ATGTTCCAAT    540
CGCATATTGC AGTTGGGCAG ATTTAAGCCT TGAGACTGAA GTAAAGTATA TTAAGGATAT    600
TAGTTCATTA ACACCGGAAG AATGGCAGTC TGGCGATAGA CGTTGGATTA TTGATTGGGT    660
AGCACCATTC GGGCATTCTC AACTACTTAT AAAAAATGTG TCAGAAATAC CTGATTACTC    720
TCGTCAGATC TATACGCTTT TATCCAAAAC AAAAAGAACT GGCAAAATTG CCTATTTTAA    780
AGGGGGGAAC TTAGATAAAA AAACAGCAAA AAAACGTTTC GATACATATC AAGAAAGGCT    840
GGGGGCAGCT CTTAAAAATG AGTTTAATTT TACTAAATAA AAGGAGACAT CCTTATGGGT    900
AAACTTGCTA ATATTTCAAC AAACTTAAAA AATTCATTGC AATCCGGTTT GCATAAAACA    960
GGGCAATCTT TAAACCAAGC CGGTCAATCT TTAAAAGCCG GAGCGAAAAA GCTCATTCTC   1020
TATATTCCAA AAGATTATGA ATATGATTCA GGAAGAGGAA ACGGTTTACA GGATTTAGTC   1080
AAAGCTGCAG AAGATTTAGG TATTGAAGTA CAAAGAGAAG AGCGTAATGG TATTGCTACC   1140
GCTCAAAACA GTTTAAGTAC AATTCAAAAT ATTCTTGGGT TTAGCGAGCG TGGAGTTGTA   1200
TTGTCTGCTC CTCAACTTGA TAAACTGCTT CAAAAATACA AAATCAGTAA AGCACCAGGT   1260
TCATCAGAAA ATGTAGCTAA AAATTTGGGT AATGCACAAA CTTTATTATC GGGTATTCAA   1320
TCTATTTTAG GCTCAGTCAT GGCCGGTATG GATTTAGATG AAATCTTGAA AAATAAAGGA   1380
```

```
AGTGAACTTG ATTTAGCAAA AGCTGGTTTA GAATTAACTA ATTCGTTAAT TGAAAATATT 1440
GCAAATTCTG TTCAAACGCT TGATACTTTT TCAGAACAAA TTAGCCAATT AGGTACTAAG 1500
TTACAAAATG TAAAAGGTTT AGGTACTTTA GGAGATAAAC TTAAAAACTT TAGTGGCTTC 1560
AGTAAAGCTG GTCTTGGCTT AGAAGTAATT TCCGGTTTGC TTTCTGGTGC AACAGCAGCT 1620
CTTGTTCTTG CAGATAAAAA TGCCTCTACA GATAGGAAAG TAGGTGCTGG CTTTGAGCTC 1680
GCAAACCAAG TTGTTGGTAA CATCACCAAA GCCGTTTCCT CTTATATTTT AGCACAGCGT 1740
GTTGCCGCGG GTTTATCTAA TACAGGCCCA GTGTCAGCAT TAATTGCTTC TACTGTAGCA 1800
CTTGCTATTA GTCCGCTTGC CTTTGCAGGA ATTGCAGATA AATTTAACAA TGCTAAAGCA 1860
CTTGAAAGTT ATGCAGAGAG ATTTAAAAAA CTAGGCTATG AGGGGGATAG TTTACTCGCT 1920
GAATATCAAC GAGGAACAGG TACGATAGAT GCTTCTGTAA CCGCGGTTAA TACTGCATTA 1980
GCTGCAATTT CAGGTGGCGT TTCAGCCGCA GCAGCCGGTT CTCTAGTCGG CGCACCGATT 2040
GCTCTACTTG TTTCTGGTAT CACCGGAATT ATCTCAACTA TTCTACAATA CTCTAAACAA 2100
GCGATGTTTG AGCATGTAGC GAATAAAATT CACGATAAAA TTGTGGATTG GGAGAAAAAA 2160
CATAACGGCA AAAACTACTT CGAAAATGGT TATGACTCTC GCTATTTAGC CGATCTTCAA 2220
GACAATATGC GTCAGTTACA GAATCTCAAT AAAGAACTAC AAGCAGAACG TGTTATCCGG 2280
ATTACGCAAC AGCAATGGGA TAATAATATT GGTAACCTGG CTGGTATCAG CCGATTAGGT 2340
GAAAAAGTAA TGAGCGGAAA AGCTTATGCA GATGCTTTTG AAGAAGGCAA ACTCATAAAA 2400
GCAGATACAT TTGTACAATT AGATTCTGCC ACAGGGGTGA TCAATACTAG CAAGTCTGAT 2460
AATGTTAAAA CTCAGCATAT TTTATTTAGA ACGCCACTAC TTACCCCAGG GGTAGAAAAT 2520
CGTGAGCGTA TTCAAACTGG TAAATATGAG TATATTACCA AATTAAATAT TAACCGTGTA 2580
GACAGCTGGA AAATTACTGA TGGAGCTACA AACTCTACCT TTGACTTGAC TAATGTGGTT 2640
CAACGTATTG GTATTGAATT AGATCACGCA GATAATGTTA CTAAAACAAA AGAGACTAAA 2700
ATTATTGCAA ATCTAGGTGA TGGCAATGAT GATGTATTTA TTGGTTCAGG CACAACTGAA 2760
GTTGATGGTG GTAACGGTCT TGATCGCGTG CATTATAGCC GAGGCGACTA CGGTGCATTA 2820
ACTATTGATG CAACGAATGA ATCAGTCCAA GGTAGTTATA CAGTTAAGCG TTTCGTTGAA 2880
ACTGGTAAAG CATTGCATGA AGTAACTGCA ACTCAATCTG TTTTAGTTGG TAGCCGCGAA 2940
GAAAAAATTG AGTATCGTCA CAGTAATAAT ACACAGCATG CTGGTTACTA TACTACAGAT 3000
ACTTTAAAGT CTGTTGAGGA AATTATTGGT ACTTCACGCA ATGATATCTT TAAAGGTAGT 3060
AAATTTGATG ATGCTTTCCA TGGCGGTGAT GGTGTTGATA ACATTGACGG TAATGCAGGC 3120
AATGACCGTC TATTTGGCGG AAAAGGCTTT GATATTATTG ATGGCGGTGA TGGTGATGAC 3180
TTTATCGATG GCGGTCAAGG AGATGATATC TTACACGGCG GCAAAGGCAA TGATATCTTG 3240
TGCACCGTCA AGGGTGGCAA TGATTCAATT AGCGACTCTG GCGGCAATGA TAGATTATCT 3300
TTCGCGGACT CAAATCTTAA AGATTTGACC TTTGAAAAAG TTAACCACCA CCTTATGATC 3360
ACTAATGTGA AAAAAGAAAA AGTAACTATT CAAAACTGGT TCCGTGAAGC CGATTATGCT 3420
AAAACTGTGC ATAATTATCA AGCAACCGCA GACGAAAAAA TTGAAGAAAT CATTGGTCGA 3480
CAAGGTGAGC GTATTACCTC TAAGCAAATT GATGAGCTGA TCGAAAAAGG TAAAGGTAAA 3540
ATTGATCAGA GTGAATTGGA GAGAATTGCT GAAAGCAGTG CTTTACTCAA AGAAAGTAAA 3600
TTTGCTTCAA ATAGCTTAAA TAAACTTGTT TCATCTGCAG CGCATTTGCC TCTTCAAACG 3660
ATAACAGAGT GGGCTTGGCG TTCCTACATC ATTGTATGAA CATACCCAAT CTGTACAATT 3720
TGTAAGAGCA GCTTAATATT TTAAATGTTT AGCAACTCTA TATTGTTTAC GCCATTATGG 3780
```

AGTTGCTATT TTATTTTTTA AAAGGAGATT TCATGGAAGT TAATCATCAA AGCCAATTGA 3840

TCTTGGAT 3848

( 2 ) INFORMATION FOR SEQ ID NO:2:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda) yfc33-37

( x i ) SEQUENCE DESCRIPTION: SEQ ID NO:2:

Ile Ile Gly Thr Ser Arg Asn Asp Ile
1 5

( 2 ) INFORMATION FOR SEQ ID NO:3:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:3:

Phe Lys Gly Ser Lys Phe Asp Asp Ala
1 5

( 2 ) INFORMATION FOR SEQ ID NO:4:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:4:

Phe His Gly Gly Asp Gly Val Asp Asn
1 5

( 2 ) INFORMATION FOR SEQ ID NO:5:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:5:

Ile Asp Gly Asn Ala Gly Asn Asp Arg
1 5

( 2 ) INFORMATION FOR SEQ ID NO:6:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:6:

Leu Phe Gly Gly Lys Gly Phe Asp Ile
1 5

( 2 ) INFORMATION FOR SEQ ID NO:7:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:7:

Ile Asp Gly Gly Asp Gly Asp Asp Phe
1 5

( 2 ) INFORMATION FOR SEQ ID NO:8:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:8:

Ile Asp Gly Gly Gln Gly Asp Asp Ile
1 5

( 2 ) INFORMATION FOR SEQ ID NO:9:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:9:

Leu His Gly Gly Lys Gly Asn Asp Ile
1 5

( 2 ) INFORMATION FOR SEQ ID NO:10:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:10:

Leu Ile Gly Thr Thr Arg Ala Asp Lys
1 5

( 2 ) INFORMATION FOR SEQ ID NO:11:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:11:

Phe Phe Gly Ser Lys Ala Phe Ala Asp
1 5

( 2 ) INFORMATION FOR SEQ ID NO:12:

( i ) SEQUENCE CHARACTERISTICS:
( A ) LENGTH: 9 amino acids ( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:12:

Phe His Gly Ala Asp Gly Asp Asp His
1 5

( 2 ) INFORMATION FOR SEQ ID NO:13:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:13:

Ile Glu Gly Asn Asp Gly Asn Asp Arg
1 5

( 2 ) INFORMATION FOR SEQ ID NO:14:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:14:

Leu Tyr Gly Asp Lys Gly Asn Asp Thr
1 5

( 2 ) INFORMATION FOR SEQ ID NO:15:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:15:

Leu Ser Gly Gly Asn Gly Asp Asp Gln
1 5

( 2 ) INFORMATION FOR SEQ ID NO:16:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:16:

Leu Tyr Gly Gly Asp Gly Asn Asp Lys
1 5

( 2 ) INFORMATION FOR SEQ ID NO:17:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:17:

Leu Ile Gly Gly Ala Gly Gly Asn Tyr
1 5

( 2 ) INFORMATION FOR SEQ ID NO:18:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:18:

Ile Ile Gly Thr Ser His Asn Asp Ile
1 5

( 2 ) INFORMATION FOR SEQ ID NO:19:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:19:

Ile Phe Lys Gly Leu Phe Met Asp Ala
1 5

( 2 ) INFORMATION FOR SEQ ID NO:20:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:20:

Phe Asn Gly Gly Asp Gly Val Asp Ala
1 5

( 2 ) INFORMATION FOR SEQ ID NO:21:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:21:

Ile Tyr Gly Asn Asp Gly Asn Asp Arg
1 5

( 2 ) INFORMATION FOR SEQ ID NO:22:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:22:

Leu Phe Gly Gly Lys Gly Asp Asp Ile
1 5

( 2 ) INFORMATION FOR SEQ ID NO:23:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:23:

Leu Asp Gly Gly Asn Gly Asp Asp Phe
1 5

( 2 ) INFORMATION FOR SEQ ID NO:24:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:24:

Ile Asp Gly Gly Lys Gly Asn Asp Leu 1 5

( 2 ) INFORMATION FOR SEQ ID NO:25:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Pasteurella haemolytica ( x i ) SEQUENCE DESCRIPTION: SEQ ID NO:25:

Leu His Gly Gly Lys Gly Asp Asp Ile
1 5

( 2 ) INFORMATION FOR SEQ ID NO:26:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:26:

Ile Ile Gly Ser Thr Leu Arg Asp Lys
1 5

( 2 ) INFORMATION FOR SEQ ID NO:27:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:27:

Phe Tyr Gly Ser Lys Phe Asn Asp Val
1 5

( 2 ) INFORMATION FOR SEQ ID NO:28:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:28:

Phe His Gly His Asp Gly Asp Asp Leu
1 5

( 2 ) INFORMATION FOR SEQ ID NO:29:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:29:

Ile Tyr Gly Tyr Asp Gly Asp Asp Arg
1 5

( 2 ) INFORMATION FOR SEQ ID NO:30:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:30:

Leu Tyr Gly Asp Asn Gly Asn Asp Glu
1 5

( 2 ) INFORMATION FOR SEQ ID NO:31:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:31:

Ile His Gly Cys Gln Gly Asn Asp Lys
1 5

( 2 ) INFORMATION FOR SEQ ID NO:32:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:32:

Leu Tyr Gly Gly Ala Gly Asn Asp Arg
1 5

( 2 ) INFORMATION FOR SEQ ID NO:33:

( i ) SEQUENCE CHARACTERISTICS:
( A ) LENGTH: 9 amino acids
( B ) TYPE: amino acid ( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:33:

Leu Phe Gly Glu Tyr Gly Asn Asn Tyr
1 5

( 2 ) INFORMATION FOR SEQ ID NO:34:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:34:

Leu Asp Gly Gly Glu Gly Asp Asp His
1 5

( 2 ) INFORMATION FOR SEQ ID NO:35:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:35:

Leu Glu Gly Gly Asn Gly Ser Asp Ile
1 5

( 2 ) INFORMATION FOR SEQ ID NO:36:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:36:

Leu Arg Gly Gly Ser Gly Asn Asp Lys
1 5

( 2 ) INFORMATION FOR SEQ ID NO:37:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:37:

Leu Phe Gly Asn Gln Gly Asp Asp Leu
1 5

( 2 ) INFORMATION FOR SEQ ID NO:38:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:38:

Leu Asp Gly Gly Glu Gly Asp Asp Gln
1 5

( 2 ) INFORMATION FOR SEQ ID NO:39:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus actinomycetemcomitans ( x i ) SEQUENCE DESCRIPTION: SEQ ID NO:39:

Leu Ala Gly Gly Glu Gly Asn Asp Phe
1 5

( 2 ) INFORMATION FOR SEQ ID NO:40:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:40:

Glu Ile Gly Ser Asn Gln Arg Asp Glu
1 5

( 2 ) INFORMATION FOR SEQ ID NO:41:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:41:

Phe Lys Gly Ser Lys Phe Arg Asp Ile
1 5

( 2 ) INFORMATION FOR SEQ ID NO:42:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:42:

Phe His Gly Ala Asp Gly Asp Asp Leu
1 5

( 2 ) INFORMATION FOR SEQ ID NO:43:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:43:

Leu Asn Gly Asn Asp Gly Asp Asp Ile
1 5

( 2 ) INFORMATION FOR SEQ ID NO:44:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:44:

Leu Tyr Gly Asp Lys Gly Asn Asp Glu
1 5

( 2 ) INFORMATION FOR SEQ ID NO:45:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:45:

Leu Arg Gly Asp Asn Gly Asn Asp Gln
1 5

( 2 ) INFORMATION FOR SEQ ID NO:46:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:46:

Leu Tyr Gly Gly Glu Gly Asp Asp Lys
1 5

( 2 ) INFORMATION FOR SEQ ID NO:47:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:47:

Leu Leu Gly Gly Asn Gly Asn Asn Tyr
1 5

( 2 ) INFORMATION FOR SEQ ID NO:48:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:48:

Leu Ser Gly Gly Asp Gly Asn Asp Glu
1 5

( 2 ) INFORMATION FOR SEQ ID NO:49:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:49:

Leu Arg Gly Gly Lys Gly Asp Asp Lys
1 5

( 2 ) INFORMATION FOR SEQ ID NO:50:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:50:

Leu Tyr Gly Ser Ser Gly Ser Asp Leu
1 5

( 2 ) INFORMATION FOR SEQ ID NO:51:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:51:

Leu Asp Gly Gly Glu Gly Asn Asp Tyr
1 5

( 2 ) INFORMATION FOR SEQ ID NO:52:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:52:

Leu Glu Gly Gly Asp Gly Ser Asp Phe
1 5

( 2 ) INFORMATION FOR SEQ ID NO:53:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:53:

Ile Ile Gly Ser Asn Arg Lys Asp Lys
1 5

( 2 ) INFORMATION FOR SEQ ID NO:54:

( i ) SEQUENCE CHARACTERISTICS:
( A ) LENGTH: 9 amino acids
( B ) TYPE: amino acid
( C ) STRANDEDNESS:

( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:54:

Phe Phe Gly Ser Arg Phe Thr Asp Ile
1 5

( 2 ) INFORMATION FOR SEQ ID NO:55:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:55:

Phe His Gly Ala Lys Gly Asp Asp Glu
1 5

( 2 ) INFORMATION FOR SEQ ID NO:56:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:56:

Leu Tyr Gly Asn Asp Gly Asn Asp Ile
1 5

( 2 ) INFORMATION FOR SEQ ID NO:57:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:57:

Leu Tyr Gly Gly Asp Gly Asn Asp Ile
1 5

( 2 ) INFORMATION FOR SEQ ID NO:58:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:58:

Ile His Gly Gly Asp Gly Asn Asp His
1 5

( 2 ) INFORMATION FOR SEQ ID NO:59:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:59:

Leu Val Gly Gly Asn Gly Asn Asp Arg
1 5

( 2 ) INFORMATION FOR SEQ ID NO:60:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:60:

Leu Ile Gly Gly Lys Gly Asn Asn Phe
1 5

( 2 ) INFORMATION FOR SEQ ID NO:61:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:61:

Leu Asn Gly Gly Asp Gly Asp Asp Glu
1 5

( 2 ) INFORMATION FOR SEQ ID NO:62:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:62:

Leu Leu Gly Gly Ala Gly Asn Asp Ile
1 5

( 2 ) INFORMATION FOR SEQ ID NO:63:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:63:

Leu Tyr Gly Ser Asp Gly Thr Asn Leu
1 5

( 2 ) INFORMATION FOR SEQ ID NO:64:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:64:

Phe Asp Gly Gly Val Gly Asn Asp Lys
1 5

( 2 ) INFORMATION FOR SEQ ID NO:65:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Actinobacillus pleuropneumoniae ( x i ) SEQUENCE DESCRIPTION: SEQ ID NO:65:

Ile Tyr Gly Gly Leu Gly Lys Asp Ile
1 5

( 2 ) INFORMATION FOR SEQ ID NO:66:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:66:

Ile Ile Gly Ser Gln Phe Asn Asp Ile
1 5

( 2 ) INFORMATION FOR SEQ ID NO:67:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:67:

Phe Lys Gly Ser Gln Phe Asp Asp Val
1 5

( 2 ) INFORMATION FOR SEQ ID NO:68:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:68:

Phe His Gly Gly Asn Gly Val Asp Thr
1 5

( 2 ) INFORMATION FOR SEQ ID NO:69:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:69:

Ile Asp Gly Asn Asp Gly Asp Asp His
1 5

( 2 ) INFORMATION FOR SEQ ID NO:70:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:70:

Leu Phe Gly Gly Ala Gly Asp Asp Val
1 5

( 2 ) INFORMATION FOR SEQ ID NO:71:

( i ) SEQUENCE CHARACTERISTICS:

( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:71:

Ile Asp Gly Gly Asn Gly Asn Asn Phe
1 5

( 2 ) INFORMATION FOR SEQ ID NO:72:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:72:

Leu Val Gly Gly Thr Gly Asn Asp Ile
1 5

( 2 ) INFORMATION FOR SEQ ID NO:73:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:73:

Ile Ser Gly Gly Lys Asp Asn Asp Ile
1 5

( 2 ) INFORMATION FOR SEQ ID NO:74:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:74:

Leu Asn Gly Gly Asp Gly Asp Asp Glu
1 5

( 2 ) INFORMATION FOR SEQ ID NO:75:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:75:

Leu Ser Gly Gly Lys Gly Asn Asp Lys
1 5

( 2 ) INFORMATION FOR SEQ ID NO:76:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:76:

Leu Tyr Gly Ser Glu Gly Ala Asp Leu
1 5

( 2 ) INFORMATION FOR SEQ ID NO:77:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:77:

Leu Asp Gly Gly Glu Gly Asn Asp Leu
1 5

( 2 ) INFORMATION FOR SEQ ID NO:78:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Escherichia coli ( x i ) SEQUENCE DESCRIPTION: SEQ ID NO:78:

Leu Lys Gly Gly Tyr Gly Asn Asp Ile
1 5

( 2 ) INFORMATION FOR SEQ ID NO:79:

( i ) SEQUENCE CHARACTERISTICS:
( A ) LENGTH: 2802 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:

( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:79:

```
ATGGGTAAAC TTGCTAATAT TTCAACAAAC TTAAAAAATT CATTGCAATC CGGTTTGCAT    60
AAAACAGGGC AATCTTTAAA CCAAGCCGGT CAATCTTTAA AAGCCGGAGC GAAAAAGCTC   120
ATTCTCTATA TTCCAAAAGA TTATGAATAT GATTCAGGAA GAGGAAACGG TTTACAGGAT   180
TTAGTCAAAG CTGCAGAAGA TTTAGGTATT GAAGTACAAA GAGAAGAGCG TAATGGTATT   240
GCTACCGCTC AAAACAGTTT AAGTACAATT CAAAATATTC TTGGGTTTAG CGAGCGTGGA   300
GTTGTATTGT CTGCTCCTCA ACTTGATAAA CTGCTTCAAA AATACAAAAT CAGTAAAGCA   360
CCAGGTTCAT CAGAAAATGT AGCTAAAAAT TTGGGTAATG CACAAACTTT ATTATCGGGT   420
ATTCAATCTA TTTTAGGCTC AGTCATGGCC GGTATGGATT TAGATGAAAT CTTGAAAAAT   480
AAAGGAAGTG AACTTGATTT AGCAAAAGCT GGTTTAGAAT TAACTAATTC GTTAATTGAA   540
AATATTGCAA ATTCTGTTCA AACGCTTGAT ACTTTTTCAG AACAAATTAG CCAATTAGGT   600
ACTAAGTTAC AAAATGTAAA AGGTTTAGGT ACTTTAGGAG ATAAACTTAA AAACTTTAGT   660
GGCTTCAGTA AAGCTGGTCT TGGCTTAGAA GTAATTTCCG GTTTGCTTTC TGGTGCAACA   720
GCAGCTCTTG TTCTTGCAGA TAAAAATGCC TCTACAGATA GGAAAGTAGG TGCTGGCTTT   780
GAGCTCGCAA ACCAAGTTGT TGGTAACATC ACCAAAGCCG TTTCCTCTTA TATTTTAGCA   840
CAGCGTGTTG CCGCGGGTTT ATCTAATACA GGCCCAGTGT CAGCATTAAT TGCTTCTACT   900
GTAGCACTTG CTATTAGTCC GCTTGCCTTT GCAGGAATTG CAGATAAATT TAACAATGCT   960
AAAGCACTTG AAAGTTATGC AGAGAGATTT AAAAAACTAG GCTATGAGGG GGATAGTTTA  1020
CTCGCTGAAT ATCAACGAGG AACAGGTACG ATAGATGCTT CTGTAACCGC GGTTAATACT  1080
GCATTAGCTG CAATTTCAGG TGGCGTTTCA GCCGCAGCAG CCGGTTCTCT AGTCGGCGCA  1140
CCGATTGCTC TACTTGTTTC TGGTATCACC GGAATTATCT CAACTATTCT ACAATACTCT  1200
AAACAAGCGA TGTTTGAGCA TGTAGCGAAT AAAATTCACG ATAAAATTGT GGATTGGGAG  1260
AAAAAACATA ACGGCAAAAA CTACTTCGAA AATGGTTATG ACTCTCGCTA TTTAGCCGAT  1320
CTTCAAGACA ATATGCGTCA GTTACAGAAT CTCAATAAAG AACTACAAGC AGAACGTGTT  1380
ATCCGGATTA CGCAACAGCA ATGGGATAAT AATATTGGTA ACCTGGCTGG TATCAGCCGA  1440
TTAGGTGAAA AAGTAATGAG CGGAAAAGCT TATGCAGATG CTTTTGAAGA AGGCAAACTC  1500
ATAAAAGCAG ATACATTTGT ACAATTAGAT TCTGCCACAG GGGTGATCAA TACTAGCAAG  1560
TCTGATAATG TTAAAACTCA GCATATTTTA TTTAGAACGC CACTACTTAC CCCAGGGGTA  1620
GAAAATCGTG AGCGTATTCA AACTGGTAAA TATGAGTATA TTACCAAATT AAATATTAAC  1680
CGTGTAGACA GCTGGAAAAT TACTGATGGA GCTACAAACT CTACCTTTGA CTTGACTAAT  1740
GTGGTTCAAC GTATTGGTAT TGAATTAGAT CACGCAGATA ATGTTACTAA AACAAAAGAG  1800
ACTAAAATTA TTGCAAATCT AGGTGATGGC AATGATGATG TATTTATTGG TTCAGGCACA  1860
ACTGAAGTTG ATGGTGGTAA CGGTCTTGAT CGCGTGCATT ATAGCCGAGG CGACTACGGT  1920
GCATTAACTA TTGATGCAAC GAATGAATCA GTCCAAGGTA GTTATACAGT TAAGCGTTTC  1980
GTTGAAACTG GTAAAGCATT GCATGAAGTA ACTGCAACTC AATCTGTTTT AGTTGGTAGC  2040
CGCGAAGAAA AAATTGAGTA TCGTCACAGT AATAATACAC AGCATGCTGG TTACTATACT  2100
ACAGATACTT TAAAGTCTGT TGAGGAAATT ATTGGTACTT CACGCAATGA TATCTTTAAA  2160
```

```
GGTAGTAAAT TTGATGATGC TTTCCATGGC GGTGATGGTG TTGATAACAT TGACGGTAAT 2220

GCAGGCAATG ACCGTCTATT TGGCGGAAAA GGCTTTGATA TTATTGATGG CGGTGATGGT 2280

GATGACTTTA TCGATGGCGG TCAAGGAGAT GATATCTTAC ACGGCGGCAA AGGCAATGAT 2340

ATCTTGTGCA CCGTCAAGGG TGGCAATGAT TCAATTAGCG ACTCTGGCGG CAATGATAGA 2400

TTATCTTTCG CGGACTCAAA TCTTAAAGAT TTGACCTTTG AAAAAGTTAA CCACCACCTT 2460

ATGATCACTA ATGTGAAAAA AGAAAAAGTA ACTATTCAAA ACTGGTTCCG TGAAGCCGAT 2520

TATGCTAAAA CTGTGCATAA TTATCAAGCA ACCGCAGACG AAAAAATTGA AGAAATCATT 2580

GGTCGACAAG GTGAGCGTAT TACCTCTAAG CAAATTGATG AGCTGATCGA AAAAGGTAAA 2640

GGTAAAATTG ATCAGAGTGA ATTGGAGAGA ATTGCTGAAA GCAGTGCTTT ACTCAAAGAA 2700

AGTAAATTTG CTTCAAATAG CTTAAATAAA CTTGTTTCAT CTGCAGCGCA TTTGCCTCTT 2760

CAAACGATAA CAGAGTGGGC TTGGCGTTCC TACATCATTG TA 2802
```

( 2 ) INFORMATION FOR SEQ ID NO:80:

( i ) SEQUENCE CHARACTERISTICS:
( A ) LENGTH: 934 amino acids
( B ) TYPE: amino acid
( C ) STRANDEDNESS:
( D ) TOPOLOGY: linear ( i i ) MOLECULE TYPE: protein ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:80:

```
Met Gly Lys Leu Ala Asn Ile Ser Thr Asn Leu Lys Asn Ser Leu Gln
1               5                   10                  15

Ser Gly Leu His Lys Thr Gly Gln Ser Leu Asn Gln Ala Gly Gln Ser
            20                  25                  30

Leu Lys Ala Gly Ala Lys Lys Leu Ile Leu Tyr Ile Pro Lys Asp Tyr
        35                  40                  45

Glu Tyr Asp Ser Gly Arg Gly Asn Gly Leu Gln Asp Leu Val Lys Ala
    50                  55                  60

Ala Glu Asp Leu Gly Ile Glu Val Gln Arg Glu Glu Arg Asn Gly Ile
65                  70                  75                  80

Ala Thr Ala Gln Asn Ser Leu Ser Thr Ile Gln Asn Ile Leu Gly Phe
                85                  90                  95

Ser Glu Arg Gly Val Val Leu Ser Ala Pro Gln Leu Asp Lys Leu Leu
            100                 105                 110

Gln Lys Tyr Lys Ile Ser Lys Ala Pro Gly Ser Ser Glu Asn Val Ala
        115                 120                 125

Lys Asn Leu Gly Asn Ala Gln Thr Leu Leu Ser Gly Ile Gln Ser Ile
    130                 135                 140

Leu Gly Ser Val Met Ala Gly Met Asp Leu Asp Glu Ile Leu Lys Asn
145                 150                 155                 160

Lys Gly Ser Glu Leu Asp Leu Ala Lys Ala Gly Leu Glu Leu Thr Asn
                165                 170                 175

Ser Leu Ile Glu Asn Ile Ala Asn Ser Val Gln Thr Leu Asp Thr Phe
            180                 185                 190
```

-continued

Ser Glu Gln Ile Ser Gln Leu Gly Thr Lys Leu Gln Asn Val Lys Gly
195 200 205

Leu Gly Thr Leu Gly Asp Lys Leu Lys Asn Phe Ser Gly Phe Ser Lys
210 215 220

Ala Gly Leu Gly Leu Glu Val Ile Ser Gly Leu Leu Ser Gly Ala Thr
225 230 235 240

Ala Ala Leu Val Leu Ala Asp Lys Asn Ala Ser Thr Asp Arg Lys Val
245 250 255

Gly Ala Gly Phe Glu Leu Ala Asn Gln Val Val Gly Asn Ile Thr Lys
260 265 270

Ala Val Ser Ser Tyr Ile Leu Ala Gln Arg Val Ala Ala Gly Leu Ser
275 280 285

Asn Thr Gly Pro Val Ser Ala Leu Ile Ala Ser Thr Val Ala Leu Ala
290 295 300

Ile Ser Pro Leu Ala Phe Ala Gly Ile Ala Asp Lys Phe Asn Asn Ala
305 310 315 320

Lys Ala Leu Glu Ser Tyr Ala Glu Arg Phe Lys Lys Leu Gly Tyr Glu
325 330 335

Gly Asp Ser Leu Leu Ala Glu Tyr Gln Arg Gly Thr Gly Thr Ile Asp
340 345 350

Ala Ser Val Thr Ala Val Asn Thr Ala Leu Ala Ala Ile Ser Gly Gly
355 360 365

Val Ser Ala Ala Ala Ala Gly Ser Leu Val Gly Ala Pro Ile Ala Leu
370 375 380

Leu Val Ser Gly Ile Thr Gly Ile Ile Ser Thr Ile Leu Gln Tyr Ser
385 390 395 400

Lys Gln Ala Met Phe Glu His Val Ala Asn Lys Ile His Asp Lys Ile
405 410 415

Val Asp Trp Glu Lys Lys His Asn Gly Lys Asn Tyr Phe Glu Asn Gly
420 425 430

Tyr Asp Ser Arg Tyr Leu Ala Asp Leu Gln Asp Asn Met Arg Gln Leu
435 440 445

Gln Asn Leu Asn Lys Glu Leu Gln Ala Glu Arg Val Ile Arg Ile Thr
450 455 460

Gln Gln Gln Trp Asp Asn Asn Ile Gly Asn Leu Ala Gly Ile Ser Arg
465 470 475 480

Leu Gly Glu Lys Val Met Ser Gly Lys Ala Tyr Ala Asp Ala Phe Glu
485 490 495

Glu Gly Lys Leu Ile Lys Ala Asp Thr Phe Val Gln Leu Asp Ser Ala
500 505 510

Thr Gly Val Ile Asn Thr Ser Lys Ser Asp Asn Val Lys Thr Gln His
515 520 525

Ile Leu Phe Arg Thr Pro Leu Leu Thr Pro Gly Val Glu Asn Arg Glu
530 535 540

Arg Ile Gln Thr Gly Lys Tyr Glu Tyr Ile Thr Lys Leu Asn Ile Asn
545 550 555 560

Arg Val Asp Ser Trp Lys Ile Thr Asp Gly Ala Thr Asn Ser Thr Phe
565 570 575

Asp Leu Thr Asn Val Val Gln Arg Ile Gly Ile Glu Leu Asp His Ala
580 585 590

Asp Asn Val Thr Lys Thr Lys Glu Thr Lys Ile Ile Ala Asn Leu Gly
595 600 605

Asp Gly Asn Asp Asp Val Phe Ile Gly Ser Gly Thr Thr Glu Val Asp
610 615 620

Gly Gly Asn Gly Leu Asp Arg Val His Tyr Ser Arg Gly Asp Tyr Gly
625 630 635 640

Ala Leu Thr Ile Asp Ala Thr Asn Glu Ser Val Gln Gly Ser Tyr Thr
645 650 655

Val Lys Arg Phe Val Glu Thr Gly Lys Ala Leu His Glu Val Thr Ala
660 665 670

Thr Gln Ser Val Leu Val Gly Ser Arg Glu Glu Lys Ile Glu Tyr Arg
675 680 685

His Ser Asn Asn Thr Gln His Ala Gly Tyr Tyr Thr Thr Asp Thr Leu
690 695 700

Lys Ser Val Glu Glu Ile Ile Gly Thr Ser Arg Asn Asp Ile Phe Lys
705 710 715 720

Gly Ser Lys Phe Asp Asp Ala Phe His Gly Gly Asp Gly Val Asp Asn
725 730 735

Ile Asp Gly Asn Ala Gly Asn Asp Arg Leu Phe Gly Gly Lys Gly Phe
740 745 750

Asp Ile Ile Asp Gly Gly Asp Gly Asp Asp Phe Ile Asp Gly Gly Gln
755 760 765

Gly Asp Asp Ile Leu His Gly Gly Lys Gly Asn Asp Ile Leu Cys Thr
770 775 780

Val Lys Gly Gly Asn Asp Ser Ile Ser Asp Ser Gly Gly Asn Asp Arg
785 790 795 800

Leu Ser Phe Ala Asp Ser Asn Leu Lys Asp Leu Thr Phe Glu Lys Val
805 810 815

Asn His His Leu Met Ile Thr Asn Val Lys Lys Glu Lys Val Thr Ile
820 825 830

Gln Asn Trp Phe Arg Glu Ala Asp Tyr Ala Lys Thr Val His Asn Tyr
835 840 845

Gln Ala Thr Ala Asp Glu Lys Ile Glu Glu Ile Ile Gly Arg Gln Gly
850 855 860

Glu Arg Ile Thr Ser Lys Gln Ile Asp Glu Leu Ile Glu Lys Gly Lys
865 870 875 880

Gly Lys Ile Asp Gln Ser Glu Leu Glu Arg Ile Ala Glu Ser Ser Ala
885 890 895

Leu Leu Lys Glu Ser Lys Phe Ala Ser Asn Ser Leu Asn Lys Leu Val
900 905 910

Ser Ser Ala Ala His Leu Pro Leu Gln Thr Ile Thr Glu Trp Ala Trp
915 920 925

Arg Ser Tyr Ile Ile Val
930

( 2 ) INFORMATION FOR SEQ ID NO:81:

( i ) SEQUENCE CHARACTERISTICS:
( A ) LENGTH: 495 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:81:

```
ATGAATCAAC ATTACTTTAA TCTATTGGGA AATATTACTT GGTTATGGAT GAACTCACCT    60
CTTCATAGAG AGTGGAGCTG TGAGCTATTG GCACGCAATG TGATTCCGGC AATTGAAAAT   120
CAACAATATA TGCTACTTAT TGATAATGAT GTTCCAATCG CATATTGCAG TTGGGCAGAT   180
TTAAGCCTTG AGACTGAAGT AAAGTATATT AAGGATATTA GTTCATTAAC ACCGGAAGAA   240
TGGCAGTCTG GCGATAGACG TTGGATTATT GATTGGGTAG CACCATTCGG GCATTCTCAA   300
CTACTTATAA AAAATGTGTC AGAAATACCT GATTACTCTC GTCAGATCTA TACGCTTTTA   360
TCCAAAACAA AAAGAACTGG CAAAATTGCC TATTTTAAAG GGGGGAACTT AGATAAAAAA   420
ACAGCAAAAA AACGTTTCGA TACATATCAA GAAAGGCTGG GGGCAGCTCT TAAAAATGAG   480
TTTAATTTTA CTAAA                                                    495
```

( 2 ) INFORMATION FOR SEQ ID NO:82:

( i ) SEQUENCE CHARACTERISTICS:
( A ) LENGTH: 165 amino acids
( B ) TYPE: amino acid
( C ) STRANDEDNESS:
( D ) TOPOLOGY: linear ( i i ) MOLECULE TYPE: protein ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:82:

```
Met Asn Gln His Tyr Phe Asn Leu Leu Gly Asn Ile Thr Trp Leu Trp
1               5                   10                  15

Met Asn Ser Pro Leu His Arg Glu Trp Ser Cys Glu Leu Leu Ala Arg
            20                  25                  30

Asn Val Ile Pro Ala Ile Glu Asn Gln Gln Tyr Met Leu Leu Ile Asp
        35                  40                  45

Asn Asp Val Pro Ile Ala Tyr Cys Ser Trp Ala Asp Leu Ser Leu Glu
    50                  55                  60

Thr Glu Val Lys Tyr Ile Lys Asp Ile Ser Ser Leu Thr Pro Glu Glu
65                  70                  75                  80

Trp Gln Ser Gly Asp Arg Arg Trp Ile Ile Asp Trp Val Ala Pro Phe
                85                  90                  95

Gly His Ser Gln Leu Leu Ile Lys Asn Val Ser Glu Ile Pro Asp Tyr
            100                 105                 110

Ser Arg Gln Ile Tyr Thr Leu Leu Ser Lys Thr Lys Arg Thr Gly Lys
        115                 120                 125

Ile Ala Tyr Phe Lys Gly Gly Asn Leu Asp Lys Lys Thr Ala Lys Lys
    130                 135                 140

Arg Phe Asp Thr Tyr Gln Glu Arg Leu Gly Ala Ala Leu Lys Asn Glu
145                 150                 155                 160

Phe Asn Phe Thr Lys
                165
```

( 2 ) INFORMATION FOR SEQ ID NO:83:

( i ) SEQUENCE CHARACTERISTICS:
( A ) LENGTH: 36 base pairs
( B ) TYPE: nucleic acid -continued ( C ) STRANDEDNESS: double
( D ) TOPOLOGY: linear ( i i ) MOLECULE TYPE: DNA (genomic)

( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:83:

ATGGAAGTTA ATCATCAAAG CCAATTGATC TTGGAT 36

( 2 ) INFORMATION FOR SEQ ID NO:84:

( i ) SEQUENCE CHARACTERISTICS:
( A ) LENGTH: 12 amino acids
( B ) TYPE: amino acid
( C ) STRANDEDNESS:
( D ) TOPOLOGY: linear ( i i ) MOLECULE TYPE: protein ( v i ) ORIGINAL SOURCE:
( A ) ORGANISM: Pasteurella suis
( B ) STRAIN: 5943

( v i i ) IMMEDIATE SOURCE:
( A ) LIBRARY: P. suis DNA in Bacteriophage lambda-dash
( B ) CLONE: (Lambda)yfc33-37

( x i ) SEQUENCE DESCRIPTION: SEQ ID NO:84:

Met Glu Val Asn His Gln Ser Gln Leu Ile Leu Asp
1 5 10